US009127039B2

(12) United States Patent
Kubota et al.

(10) Patent No.: US 9,127,039 B2
(45) Date of Patent: Sep. 8, 2015

(54) SULFUR-CONTAINING AMINO ACID DERIVATIVE

(71) Applicant: AJINOMOTO CO., INC., Tokyo (JP)

(72) Inventors: Kazuyuki Kubota, Kanagawa (JP); Toshimi Mizukoshi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 13/678,805

(22) Filed: Nov. 16, 2012

(65) Prior Publication Data

US 2013/0071863 A1    Mar. 21, 2013

Related U.S. Application Data

(63) Continuation of application No. PCT/JP2011/061460, filed on May 18, 2011.

(30) Foreign Application Priority Data

May 18, 2010    (JP) ................. 2010-114616

(51) Int. Cl.
| | |
|---|---|
| C07K 16/00 | (2006.01) |
| G01N 33/53 | (2006.01) |
| C07K 5/062 | (2006.01) |
| G01N 33/68 | (2006.01) |
| C07K 16/44 | (2006.01) |
| C07K 5/065 | (2006.01) |
| C12N 5/16 | (2006.01) |
| C07K 16/46 | (2006.01) |

(52) U.S. Cl.
CPC ........... *C07K 5/06026* (2013.01); *C07K 5/0606* (2013.01); *C07K 5/06034* (2013.01); *C07K 5/06078* (2013.01); *C07K 16/44* (2013.01); *G01N 33/68* (2013.01); *G01N 33/6806* (2013.01); *G01N 33/6812* (2013.01); *C07K 16/468* (2013.01); *C12N 5/16* (2013.01); *G01N 33/6815* (2013.01)

(58) Field of Classification Search
CPC ........... G01N 33/6812; G01N 33/6815; C07K 16/44; C07K 16/468
See application file for complete search history.

(56) References Cited

U.S. PATENT DOCUMENTS

| | | | | |
|---|---|---|---|---|
| 4,859,613 | A * | 8/1989 | Lawrence ..................... | 436/548 |
| 4,990,443 | A | 2/1991 | Huber et al. | |
| 5,492,841 | A | 2/1996 | Craig | |
| 7,833,798 | B2 | 11/2010 | Kubota et al. | |

FOREIGN PATENT DOCUMENTS

| | | |
|---|---|---|
| EP | 0161107 | 11/1985 |
| JP | 61-34466 | 2/1986 |
| JP | 2-138293 | 5/1990 |
| JP | 07-107992 | 4/1995 |
| JP | 07-260784 | 10/1995 |
| JP | 08-211054 | 8/1996 |
| JP | 2000-055917 | 2/2000 |
| JP | 2001-255324 | 9/2001 |
| JP | 2001-272401 | 10/2001 |
| JP | 2004-279412 | 10/2004 |
| WO | WO2011/145664 | 11/2011 |

OTHER PUBLICATIONS

Hirose et al. Isolation of anti-glutathione antibodies from a phage display library. Protein Engineering 1998. vol. 11, No. 3, pp. 243-248.*

Fujiwara et al. Monoclonal antibody monospecific to glycine for branin immunocytochemistry. Brain Research 1998, vol. 806, pp. 210-218.*

Hirose et al. Isolation of anti-glutathione antibodies from a phage display library. Protein Engineering, 1998, vol. 11, No. 3, pp. 243-248.*

Grathaus et al. Taxane-specific monoclonal antibodies: measurement of taxol, baccatin III, and "total taxanes" in *Taxus brevifolia* extracts by enzyme immunoassay. Jorrnal of Natural Products 1995, vol. 58, No. 7, pp. 1003-1014.*

Saido, T., "Production of anti-peptidic antibodies distinguishing a proteolytic fragment from intact substrate polypeptide," Exp. Med. 1997;15(8):927-931.

Omi, S., "Laboratory Hitokuchi Memo (27) Mijikai Peptide, Men'eki suru Toki Doshitemasuka?" Cell Technol. 1997;16(9):1378-1380.

Kobayashi, N., et al., "Idiotype-anti-idiotype-based noncompetitive enzyme-linked immunosorbent assay of ursodeoxycholic acid 7-$N$-acetylglucosaminides in human urine with subfemtomole range sensitivity," J. Immunol. Methods 2003;272:1-10.

Liu, C.-j., et al., "Glutamate-like immunoreactivity revealed in rat olfactory bulb, hippocampus and cerebellum by monoclonal antibody and sensitive staining method," Histochem. 1989;90:427-445.

Schulze, F., et al., "Determination of asymmetric dimethylarginine (ADMA) using a novel ELISA assay," Clin. Chem. Lab. Med. 2004;42(12):1377-1383.

International Search Report for PCT Patent App. No. PCT/JP2011/061460 (Aug. 23, 2011).

International Preliminary Report on Patentability for PCT Patent App. No. PCT/JP2011/061460 (Dec. 10, 2012).

* cited by examiner

*Primary Examiner* — Shafiqul Haq

(74) *Attorney, Agent, or Firm* — Shelly Guest Cermak; Cermak Nakajima & McGowan LLP

(57) ABSTRACT

The present invention provides a method of measuring an endogenous low-molecular-weight compound specifically and conveniently with high sensitivity. Using the particular sulfur-containing amino acid derivative, a method of measuring an endogenous low-molecular-weight compound specifically and conveniently with high sensitivity can be provided.

9 Claims, 4 Drawing Sheets

SULFUR-CONTAINING AMINO ACID DERIVATIVE

This application is a Continuation of, and claims priority under 35 U.S.C. §120 to, International Application No. PCT/JP2011/061460, filed May 18, 2011, and claims priority therethrough under 35 U.S.C. §119 to Japanese Patent Application No. 2010-114616, filed May 18, 2010, the entireties of which are incorporated by reference herein.

BACKGROUND OF THE INVENTION

1. Technical Field

The present invention relates to a sulfur-containing amino acid derivative. Furthermore, the present invention relates to a reagent containing the sulfur-containing amino acid derivative, an antibody recognizing an endogenous low-molecular-weight compound using the sulfur-containing amino acid derivative and a method for producing this antibody, and a method of measuring an endogenous low-molecular-weight compound using the sulfur-containing amino acid derivative.

2. Background Art

A non-competitive method for immunologically measuring low-molecular-weight compounds has been reported (JP-A-8-211054). According to this report, an animal can be immunized with an antigen-antibody complex of hapten (antigen), and an antihapten antibody (the first antibody) as an immunogen, and a new second antibody capable of recognizing the complex can be obtained. The principle of the measurement method is that the first antibody is immobilized on a carrier, an antigen-antibody reaction with hapten occurs, and then the labeled second antibody is bound thereto. However, at least two kinds of antibodies are necessary for this method, which increases the time and cost required for these types of measurements. In addition, at least two antibodies having high selectivity to the antigen need to be prepared. While there are other reports on the detection or measurement of a low-molecular-weight compound (JP-A-2000-55917, J. Immunological. Met. 272, 1-10 (2003), Histochemistry 90, 427-445 (1989) and Clin. Chem. Lab. Med. 42, 1377-1383 (2004)), multiple kinds of antibodies are necessary, as in the above-mentioned methods, and sufficient sensitivity to permit quantification of a low-molecular-weight compound cannot be obtained.

There are two factors that can prevent production of an antibody with sufficient affinity for a low-molecular-weight compound, particularly an endogenous low-molecular-weight compound. One of them is the size of epitope. Generally, the epitope size is thought to be about 3-8 amino acid residues. Therefore, when the low-molecular-weight compound is an amino acid, it is difficult to obtain an anti-amino acid antibody recognizing, for example, one amino acid residue, and even if it can be obtained, the affinity is considered to be low. The other factor is that an immune response to an endogenous compound such as amino acid does not generally occur easily.

Generally, there are two types of immunoassays that can be used to examine an antigen-antibody reaction: a competitive immunoassay and a non-competitive immunoassay. In the competitive immunoassay, an antigen in a sample and a given amount of a labeled antigen competitively bind to an antibody immobilized in a given amount on a carrier. That is, when the amount of an antigen in a sample is small, the amount of binding between a labeled antigen and the antibody increases, and high signal intensity is observed. When the amount of the antigen in a sample is high, low signal intensity is observed conversely. On the other hand, as a non-competitive immunoassay, the sandwich immunoassay is known. In the sandwich immunoassay, an antigen-containing sample is added to excess amount of an antibody (the first antibody) immobilized on a carrier and then a labeled antibody (the second antibody) is added. While the first and second antibodies recognize the same antigen, since each antibody recognizes a different site of the antigen surface, one antigen is sandwiched between the two antibodies to form a sandwich-type binding pattern. As a result, the signal increases consistent with the amount of the antigen, which enables a quantitative analysis of the antigen amount.

In general, in a competitive immunoassay, a reaction time of a few hours to one night is required for bonding form (B) and free form (F) to reach equilibrium in an antigen-antibody reaction. In a competitive immunoassay, when an unlabeled antigen and a labeled antigen show different affinities for an antibody, the accuracy of the analysis values may decrease.

In contrast, in a non-competitive immunoassay, the reaction time can be shortened, and a measurement method with a wide measurement concentration range can be constructed since the antigen amount corresponds to the amount of the labeled antibody. During an antigen-antibody reaction, two antibodies are present in excess amounts relative to the antigen amount. Thus, the equilibrium shown by the formula (1) is directed toward formation of a complex, under which environment even a trace amount of antigen can form a complex with ease. As a result, a non-competitive immunoassay enables highly sensitive measurements as compared to a competitive immunoassay.

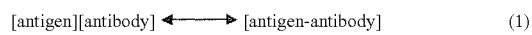

[antigen][antibody] ⇌ [antigen-antibody]     (1)

However, as mentioned above, in a sandwich type non-competitive immunoassay, two kinds of antibodies are necessary for one antigen. These antibodies need to recognize different regions of the antigen. Therefore, when an antigen is a low-molecular-weight compound, it is difficult to obtain two antibodies with different recognition sites due to the small molecular size. Thus, it is difficult to use a non-competitive immunoassay for the measurement of a low-molecular-weight compound.

SUMMARY OF THE INVENTION

It is an aspect of the present invention to provide a method of measuring an endogenous low-molecular-weight compound specifically and conveniently with high sensitivity.

It is an aspect of the present invention to provide a method of using a sulfur-containing amino acid derivative.

It is an aspect of the present invention to provide a sulfur-containing amino acid derivative comprising a structure represented by the following formula (I):

wherein X is an immunoresponsive hydrophobic group, Y is selected from the group consisting of an endogenous low-molecular-weight compound reactive group and a group bound to an endogenous low-molecular-weight compound, Z is selected from the group consisting of a hydrogen atom, a high-molecular-weight-imparting group, and a labeling compound modifying group, and A is a single bond or a $C_{1-6}$ alkylene group.

It is a further aspect of the present invention to provide the derivative as described above, wherein Y is a group bound with an endogenous low-molecular-weight compound, and Z is selected from the group consisting of a hydrogen atom and a high-molecular-weight-imparting group.

It is a further aspect of the present invention to provide the derivative as described above, wherein Y is an endogenous low-molecular-weight compound reactive group, and Z is a labeling compound modifying group.

It is a further aspect of the present invention to provide the derivative as described above, wherein the immunoresponsive hydrophobic group has a cyclic structure.

It is a further aspect of the present invention to provide the derivative as described above, wherein the immunoresponsive hydrophobic group is selected from the group consisting of a 9-fluorenylmethyloxycarbonyl (Fmoc) group and a quinolinylaminocarbonyl group.

It is a further aspect of the present invention to provide the derivative as described above, wherein the endogenous low-molecular-weight compound reactive group is selected from the group consisting of an aldehyde group, an N-succinimidyl group, a halogen group, an isothiocyanate group, and a maleimido group.

It is a further aspect of the present invention to provide the derivative as described above, wherein the high-molecular-weight-imparting group or labeling compound modifying group is bound via a linker.

It is a further aspect of the present invention to provide a reagent for measuring an endogenous low-molecular-weight compound, which comprises the sulfur-containing amino acid derivative as described above.

It is a further aspect of the present invention to provide the reagent as described above, wherein the endogenous low-molecular-weight compound is an amino acid.

It is a further aspect of the present invention to provide a method of producing an antibody which is able to recognize an endogenous low-molecular-weight compound, comprising a step of immunizing an animal with an antigen comprising the sulfur-containing amino acid derivative as described above.

It is a further aspect of the present invention to provide an antibody which is able to recognize an endogenous low-molecular-weight compound produced by a method using an antigen comprising the sulfur-containing amino acid derivative as described above.

It is a further aspect of the present invention to provide the antibody as described above, wherein the antibody is a monoclonal antibody.

It is a further aspect of the present invention to provide a method of measuring an endogenous low-molecular-weight compound in a body, comprising:

(A) reacting the derivative as described above with a test sample to form a coupling product of the derivative and an endogenous low-molecular-weight compound present in the test sample, (B) contacting the coupling product formed in step (A) with the antibody as described above, resulting in a coupling product-antibody complex, (C) measuring a label bound to the coupling product in the coupling product-antibody complex of step (B).

EFFECT OF THE INVENTION

Using the sulfur-containing amino acid derivative in accordance with the presently described subject matter, a method of measuring an endogenous low-molecular-weight compound specifically and conveniently with high sensitivity can be provided.

DESCRIPTION OF THE PREFERRED EMBODIMENTS

1. Sulfur-Containing Amino Acid Derivative

Figure 1:
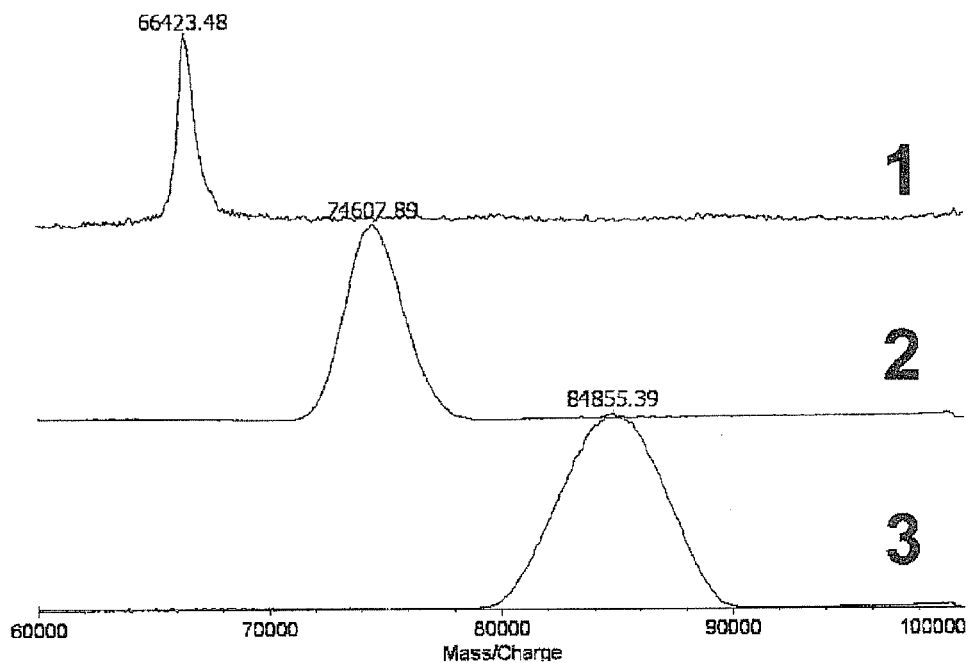
FIG. 1 shows MALDI-TOF MS spectra of BSA and a conjugate of BSA and various haptens, wherein 1 shows a spectrum of chemically-unmodified BSA, 2 shows a spectrum of maleimido-activated BSA, and 3 shows a spectrum of a conjugate of maleimido-activated BSA and Fmoc-Cys[H]-Gly.

A novel sulfur-containing amino acid derivative is described, particularly a compound which can be used to measure the amount of an endogenous low-molecular-weight compound present in a body or a sample. The sulfur-containing amino acid derivative can be a sulfur atom-containing amino acid, which has been modified to the extent the structure and properties of the base are not drastically changed, by introduction of a functional group, substitution of atom, and the like. More specifically, the derivative can be a compound having a structure represented by the following formula (I):

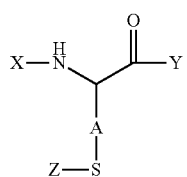

(I)

wherein X is an immunoresponsive hydrophobic group, Y is an endogenous low-molecular-weight compound reactive group or a group bound with an endogenous low-molecular-weight compound, Z is a hydrogen atom, a high-molecular-weight-imparting group or a labeling compound modifying group, and A is a single bond or an alkylene group having 1-6, 1-5, 1-4, 1-3, or 1 or 2 carbon atoms.

Furthermore, the derivative as described above can be a compound having a structure represented by formula (I), and Y can be a group bound to an endogenous low-molecular-weight compound, and Z can be a hydrogen atom or a high-molecular-weight-imparting group (this compound is also called compound (II)).

In compound II, when Z is a hydrogen atom, the compound can be used as a hapten or antigen bound to an antibody recognizing an endogenous low-molecular-weight compound. Furthermore, in compound II, when Z is a high-molecular-weight-imparting group, the compound can be used as an antigen (immunogen) to produce the antibody.

Moreover, the derivative as described above can be a compound having a structure represented by formula (I), and Y can be an endogenous low-molecular-weight compound reactive group, and Z can be a labeling compound modifying group (this compound is also called compound (III)).

A compound such as compound III can be a conjugate of an endogenous low-molecular-weight compound and the target of a measurement, and can be used as a signal probe capable of detecting the endogenous low-molecular-weight compound. The compound can be mainly used in the below-mentioned measurement method for measuring an endogenous low-molecular-weight compound.

The sulfur-containing amino acid derivatives represented by the above-mentioned compounds (I), (II), and (III) are, as mentioned above, useful as reagents in methods for the measurement of an endogenous low-molecular-weight compound, particularly for immunological measurement, and the present invention also provides such reagents.

The above-mentioned compounds (I), (II), and (III) can be optical isomers of (R)-form and (S)-form based on an asymmetric carbon, and the compounds can include any considerable optically active form and mixtures thereof (e.g., racemate, enantiomer mixture, diastereomer mixture etc.).

In the above-mentioned compounds (I), (II), and (III), X can be an immunoresponsive hydrophobic group which is a hydrophobic group that can improve immune responsiveness, wherein the compound is exogenous. A "hydrophobic group" can mean a group having low polarity and low affinity for water molecules, and is specifically a hydrocarbon group such as an alkyl group and the like.

There are 3 objectives for the introduction of an immunoresponsive hydrophobic group. The first is to increase the molecular weight of the sulfur-containing amino acid derivative. This is because when a hapten is a single amino acid, its size is not sufficient as an epitope and production of a high affinity antibody can be difficult. While the molecular weight to be increased is not particularly limited, it can be, for example, not less than 70, or not less than 120. The second objective is to increase the affinity of the antigen-antibody reaction. When the immunoresponsive hydrophobic group to be introduced into the moiety of X has an aromatic ring, an alkyl group, and the like, and the antibody recognizes the X moiety as well, the affinity of an antigen-antibody reaction can be increased by the effect of the hydrophobic interaction. The third objective is to increase the immune responses. Since an endogenous compound is a substance inherently present in the body, immune responsiveness to the compound is generally low. In contrast, when the structure of the immunoresponsive hydrophobic group is exogenous, the immunogenicity increases to promote an immune response, thus increasing production of the antibody.

While the immunoresponsive hydrophobic group is not particularly limited as long as it increases the molecular weight of the sulfur-containing amino acid derivative, increases the affinity of an antigen-antibody reaction, and improves the immune responsiveness of a test animal immunized with an antigen containing the sulfur-containing amino acid derivative, it can be a group having a cyclic structure. As a group having a cyclic structure, a group containing a hydrocarbon ring can be mentioned. A group containing a hydrocarbon ring is a group containing a structure wherein carbon atoms are bonded to form a ring, and the structure may be a monocyclic hydrocarbon or a condensed polycyclic hydrocarbon. As the monocyclic hydrocarbon, cyclopropane, cyclobutane, cyclopentane, cyclohexane, cyclobutene, cyclopenta-2,4-diene, and the like, and as the condensed polycyclic hydrocarbon, pentalene, indene, naphthalene, azulene, biphenylene, fluorene, anthracene, tetracene, triphenylene, and the like can be mentioned. In addition, the group having a cyclic structure may contain a hetero atom (hetero ring). As the hetero ring, monocyclic hetero rings such as pyrrole, furan, thiophene, imidazole, oxazole, thiazole, pyrazole, isoxazole, isothiazole, pyridine, pyridazine, pyrimidine, pyrazine, piperidine, morpholine, and the like, and fused hetero rings such as isobenzofuran, 1,3-dihydroisobenzofuran, phthalan, phthalide, phthalidyl, benzofuran, isochromen, isochromenylium, 2H-chromene, 9H-xanthene, xanthilium, oxanthrene, and the like can be mentioned. The group having the cyclic structure can be a group containing an aromatic ring or an alkyl group having a carbon number of 1-10 and the like. As the aromatic ring, benzene, naphthalene, anthracene, furan, benzofuran, and the like can be mentioned. As the alkyl group having a carbon number of 1-10, methyl group, ethyl group, propyl group, isopropyl group, butyl group, isobutyl group, sec-butyl group, tert-butyl group, pentyl group, hexyl group, heptyl group, octyl group, nonyl group, decanyl group, and the like can be mentioned. The above-mentioned alkyl group may be linear or branched chain, an alkyl group can have a carbon number of 3-10, or 5-10. The immunoresponsive hydrophobic group can have a fused ring to increase the molecular weight, improve the affinity of antigen-antibody reaction, and improve the immune responsiveness of a test animal. Examples of the immunoresponsive hydrophobic group can include 9-fluorenylmethyloxycarbonyl (Fmoc) group, quinolinylaminocarbonyl group, 4-N,N-dimethylaminosulfonyl-7-piperazino-2,1,3-benzoxadiazole (DBD-PZ group), 4-fluoro-7-nitrobenzo-2-oxa-1,3-diazole (NBD-F group), 5-N,N-dimethylaminonaphthalenesulfonyl chloride (DNS-Cl group), o-phthalaldehyde (OPA group) and 4-phenylspiro[furan-2(3H),1'-phthalan]-3,3'-dione (fluorescamine group), N,N,N-trimethylammonioanilyl N'-hydroxysuccinimidyl carbamate iodide (TAHS group), fluorescein group, dansyl chloride group, and the like. Of these, the Fmoc group and the quinolinylaminocarbonyl group are particular examples.

The Y group in the above-mentioned compounds can be endogenous low-molecular-weight compound reactive groups (hereinafter to be sometimes referred to as "Y1 group") or groups bound to an endogenous low-molecular-weight compound (hereinafter to be sometimes referred to as "Y2 group"). An active group which is reactive with an endogenous low-molecular-weight compound, which is the measurement target, can be introduced into the endogenous low-molecular-weight compound reactive group (Y1 group). Although with no particular limitation, when the Y1 group contains groups that are reactive with amino groups, for example, an aldehyde group, N-succinimidyl group, halogen group (e.g., F, Cl, Br etc.), isothiocyanate group, and the like, the Y1 group can easily react with an endogenous low-molecular-weight compound containing an amino group resulting in the binding of the endogenous low-molecular-weight compound to the sulfur-containing amino acid derivative. When the Y1 group contains groups that are reactive with a carboxyl group, for example, an amino group (—NH$_2$), the Y1 can easily react with an endogenous low-molecular-weight compound containing carboxylic acid (carboxyl group) resulting in the binding of the endogenous low-molecular-weight compound to the sulfur-containing amino acid derivative. In addition, when the Y1 group contains a group that reacts with a thiol group, for example, a maleimido group, the Y1 group can easily react with an endogenous low-molecular-weight compound containing a thiol group resulting in the binding of the endogenous low-molecular-weight compound to the sulfur-containing amino acid derivative. Moreover, when the Y1 group contains, for example, a hydrazine group, it can easily react with an endogenous low-molecular-weight compound that contains a sugar structure, resulting in the binding of the endogenous low-molecular-weight compound to the sulfur-containing amino acid derivative. As a result, various endogenous low-molecular-weight compounds such as amino acids, peptides, organic acids, free fatty acids, sugars, sugar phosphates, nucleic acids, and the like can be introduced into the Y1 group moiety of the sulfur-containing amino acid derivative. The Y2 group can be a group formed by the reaction of a Y1 group and an endogenous low-molecular-weight compound as mentioned above, wherein the endogenous low-molecular-weight compound has a chemical structure which can act as a target for measurement. Thus, it can be utilized for the production of an antibody to the endogenous low-molecular-weight compound.

The Z moiety in the above-mentioned compounds (I), (II), and (III) can be a hydrogen atom, a high-molecular-weight-imparting group, or a labeling compound modifying group. The high-molecular-weight-imparting group can be introduced to increase the molecular weight of the above-mentioned compounds, and a group with low immunogenicity for the immunization target animal is one particular example. A labeling compound modifying group can be introduced to label the above-mentioned compounds (I) or (III). When Z is a hydrogen atom, the sulfur-containing amino acid derivative can be a hapten. When Z is a high-molecular-weight-imparting group, the sulfur-containing amino acid derivative can be used as an immunogen for producing an antibody. When the prepared immunogen is regularly administered multiple times to an animal such as a mouse, guinea pig, rat, goat, monkey, Macaca mulatta, dog, rabbit, bovine, chicken, cat, hamster, sheep, swine, camel, and the like, an immune response is developed, and an antibody which recognizes a region of the molecule on the surface of an immunogen, namely, the immunoresponsive hydrophobic group and/or the endogenous low-molecular-weight compound in the sulfur-containing amino acid derivative, can be produced. As the high-molecular-weight-imparting group, a carrier protein can be used, for example, bovine serum albumin (BSA), rabbit serum albumin (RSA), ovalbumin (OVA), keyhole-limpet hemocyanin (KLH), thyroglobulin (TG), immunoglobulin, and the like can be mentioned. When employing a carrier protein, the high-molecular-weight-imparting group can also be referred to as a "carrier protein binding group". In addition, a synthetic polymer can also be used as the high-molecular-weight-imparting group and, for example, various latexes and the like, such as polymer substances, copolymeric substances, and the like, such as polyamino acids, polystyrenes, polyacryls, polyvinyls, polypropylenes, and the like can be mentioned. When these substances are used, the high-molecular-weight-imparting group can also be referred to as a "synthetic polymer binding group". One high-molecular-weight-imparting group (Z) can contain one or more moieties capable of binding to a moiety represented by the following formula (1):

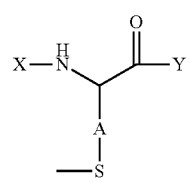

(1)

wherein X is an immunoresponsive hydrophobic group, Y is an endogenous low-molecular-weight compound reactive group or a group bound to an endogenous low-molecular-weight compound, and A is a single bond or a $C_{1-6}$ alkylene group, or a moiety as described above in formula (1), but wherein Y is a group bound with an endogenous low-molecular-weight compound (this can also be referred to as formula (2)). An embodiment wherein two or more of the above-mentioned moieties are bound is also encompassed.

In addition, the high-molecular-weight-imparting group can be bound to a sulfur atom via a linker in the above-mentioned formula (1) or (2). The surface presentation capacity of the antigen moiety increases by binding the high-molecular-weight-imparting group via a linker rather than by directly binding a polymeric compound and a sulfur atom, and therefore, an antibody having higher specificity can be produced. While the linker that can be used is not particularly limited as long as it can be used to improve the antigen presentation capacity, for example, a linker that crosslinks an amino group and a sulfur atom is a particular example. For example, maleimidobutyrylsuccinimido (MBS), maleimidocaproylsuccinimido (MCS), maleimidoundecanoylsuccinimido (MUS), sulfosuccinimidyl 4-(N -maleimidomethyl) cyclohexane-1-carboxylate(sulfo-SMCC) and the like are known.

On the other hand, when Z is a labeling compound modifying group, the sulfur-containing amino acid derivative can be utilized as a signal probe for detecting the presence of an endogenous low-molecular-weight compound. In the above-mentioned compounds (I) or (III), a labeling compound modifying group may be bound via a linker similar to the above-mentioned high-molecular-weight-imparting group. The labeling compound modifying group can be a group used to introduce a labeling compound such as enzyme (Horse-Radish peroxidase (HRP), alkaline phosphatase (AP), β-galactosidase, luciferase etc.), fluorescent substance (fluorescamine, fluorescein isothiocyanate (FITC), phycoerythrin (PE), allophycocyanin (APC), green fluorescent protein (GFP) etc.), ($^{125}$I, $^{131}$I, $^{3}$H, $^{32}$S, $^{14}$C etc., radioactive isotope) stable isotope, dye, metal, colloid, magnetic material, and the like into the above-mentioned compounds (I) or (III). A labeling compound modifying group may be introduced via biotin or lectin, and the like, instead of by direct introduction. Since biotin is a molecule that selectively reacts with avidin or streptavidin, for introduction of biotin, avidin or streptavidin only needs to be labeled in advance. Lectin can also afford a similar effect by labeling saccharides in advance that selectively react therewith.

In the above-mentioned compounds, A can be a single bond or a $C_{1-6}$ alkylene group. The $C_{1-6}$ alkylene group can be a linear or branched chain alkylene group having a carbon number of 1-6, 1-5, 1-4, 1-3, or 1 or 2. Specifically, methylene, ethylene, trimethylene, propylene, isopropylene, butylene, isobutylene, pentylene, n-hexylene, and the like can be mentioned.

The endogenous low-molecular-weight compound, which is the measurement target, can be a low-molecular-weight compound derived from a living organism, which generally has a molecular weight of 1000 or below. The endogenous low-molecular-weight compound only needs to be a low-molecular-weight compound which is present in the body. For example, the endogenous low-molecular-weight compound can include a low-molecular-weight compound artificially produced by a synthetic method etc., as long as the low-molecular-weight compound is present in a living organism or body. Examples of the endogenous low-molecular-weight compound can include an amino acid, organic acid, sugar, sugar phosphate, nucleic acid, free fatty acid, oligopeptide (dipeptide, tripeptide, tetrapeptide, pentapeptide, hexapeptide etc.), and the like.

Examples of the amino acid include glycine, alanine, valine, norvaline, leucine, isoleucine, norleucine, phenylglycine, phenylalanine, methionine, cysteine, cystine, homocysteine, homocystine, glutamine, asparagine, glutamic acid, aspartic acid, lysine, ornithine, hydroxylysine, arginine, histidine, 1-methylhistidine, 3-methylhistidine, proline, hydroxyproline, serine, threonine, tryptophan, tyrosine, citrulline, β-alanine, thyroxine, sarcosine, creatinine, γ-aminobutyric acid, and derivatives thereof, and the like.

Examples of the organic acid include lactic acid, citric acid, cis-aconitic acid, isocitric acid, 2-oxoglutaracid, succinic acid, fumaric acid, malic acid, oxaloacetic acid, maleic acid, maleic anhydride, and derivatives thereof, and the like.

Examples of the sugar include glucose, sucrose, fructose, lactose, maltose, trehalose, N-acetylglucosamine, raffinose, acarbose, and the like.

Examples of the sugar phosphate include glucose-1-phosphate, glucose-6-phosphate, fructose-6-phosphate, 1,3-bisphosphoglycerate, fructose-1,6-bisphosphate, glyceraldehyde-3-phosphate, dihydroxyacetone phosphate, 3-phosphoglycerate, 2-phosphoglycerate, phosphoenolpyruvic acid, and the like.

Examples of the nucleic acid include adenine, adenosine, adenosine monophosphate, adenosine diphosphate, adenosine triphosphate, deoxyadenosine monophosphate, deoxyadenosine diphosphate, deoxyadenosine triphosphate, guanine, guanosine, guanosine monophosphate, guanosine diphosphate, guanosine triphosphate, deoxyguanosine monophosphate, deoxyguanosine diphosphate, deoxyguanosine triphosphate, thymine, thymidine, 5-methyluridine monophosphate, 5-methyluridine diphosphate, 5-methyluridine triphosphate, thymidine monophosphate, thymidine diphosphate, thymidine triphosphate, cytosine, cytidine, cytidine monophosphate, cytidine diphosphate, cytidine triphosphate, deoxycytidine monophosphate, deoxycytidine diphosphate, deoxycytidine triphosphate, uracil, uridine, uridine monophosphate, uridine diphosphate, uridine triphosphate, deoxyuridine monophosphate, deoxyuridine diphosphate, deoxyuridine triphosphate, and the like.

Examples of the free fatty acid include butyric acid, valeric acid, caproic acid, enanthic acid, caprylic acid, pelargric acid, capric acid, lauric acid, myristic acid, pentadecylic acid, palmitic acid, pulmitoleic acid, margaric acid, stearic acid, oleic acid, vaccenic acid, linoleic acid, linolenic acid, eleostearic acid, tuberculostearic acid, arachidic acid, arachidonic acid, behenic acid, lignoceric acid, nervonic acid, cerotic acid, montanic acid, melissic acid, or these derivatives, and the like.

Examples of the oligopeptide include carnosine (β-alanyl -L-histidine), homoanserine (β-alanyl-N-methylhistidine), homoserine (N-(4-aminobutyryl)-L-histidine), and the like.

Of these endogenous low-molecular-weight compounds, amino acids are particular examples since amino acids can be used to conveniently assess the health condition of an animal. As the amino acid, neutral amino acids, acidic amino acids, and basic amino acids can be mentioned. To assess the health index of an animal, a neutral amino acid is a particular example, branched chain amino acid (leucine, isoleucine or valine) or aromatic amino acid (phenylalanine or tyrosine) is another example, and an aromatic amino acid (phenylalanine or tyrosine) is a further example. The amino acid can include an L form, D form, and DL form, and the asymmetric center of the amino acid may be in the R-configuration, S-configuration and/or RS-configuration.

The production method of the sulfur-containing amino acid derivative is not particularly limited, and the production method may vary depending on the starting material. The basic compound for the synthesis of the sulfur-containing amino acid derivative is not particularly limited as long as it contains an amino group, a carboxyl group, or a thiol group. For example, a compound similar to cysteine or cysteine can be used. The starting material may be any of, for example, (A) a basic compound having an endogenous low-molecular-weight compound already bound to a carboxyl group thereof, (B) a basic compound having an immunoresponsive hydrophobic group already bound to the amino group thereof, and (C) a basic compound wherein amino group, carboxyl group and thiol group are unmodified.

When (A) is used as the starting material, for example, a compound having a reactive group that easily reacts with an amino group such as 9-fluorenylmethyl N-succinimidyl carbonate, 6-aminoquinolyl-N-hydroxysuccinimidyl carbamate, and the like (hereinafter to be referred to as an immunoresponsive hydrophobic group containing compound) can be mixed under neutral to basic (pH 7 to 11) conditions at 4 to 80° C. and reacted for 1 min to 24 hr, resulting in the introduction of the immunoresponsive hydrophobic group into the starting material.

When (B) is used as the starting material, for example, the starting material is dissolved in water or an organic solvent, and mixed with, in a non-aqueous solvent, N-hydroxysuccinimide (NHS) and the like capable of binding to an endogenous low-molecular-weight compound, and a condensation reaction can be performed in the presence of a condensing agent such as DCC, DIC, EDC, DIPCDI, HATU, HBTU, DMT-MM, and the like at 4 to 60° C. for 30 to 240 min. As a result, an N-succinimidyl group can be introduced as an endogenous low-molecular-weight compound reactive group (Y1 group) into a carboxyl group of the starting material. Thereafter, an endogenous low-molecular-weight compound containing an amino group is mixed under neutral to basic (pH 7 to 11) conditions at 4 to 80° C. and the reaction is performed for 1 min to 24 hr, resulting in the introduction of a group (Y2 group) bound to an endogenous low-molecular-weight compound into the carboxyl group of the starting material. When an aldehyde group, halogen group (e.g., F, Cl, Br etc.), isothiocyanate group, and the like are introduced into the Y1 group moiety instead of the N-succinimidyl group, for example, a compound containing an aldehyde group, halogen group, isothiocyanate group, and the like only needs to be reacted with the starting material. When an amino group (—NH$_2$) is introduced into the Y1 group, for example, a compound having two amino groups such as ethylenediamine is reacted to allow one of the two amino groups to be bound to the carboxyl group of the starting material. Consequently, the other free amino group is reacted with a carboxylic acid-containing endogenous low-molecular-weight compound. Furthermore, when, for example, a compound having an amino group and a maleimido group is reacted with the starting material, the Y1 group contains a maleimido group. When, for example, a compound having an amino group and a hydrazine group is reacted with the starting material, the Y1 group contains a hydrazine group. The reaction between the above-mentioned various compounds and a starting material can be performed under conditions similar to those used for the above-mentioned N-hydroxysuccinimide. In addition, by reacting an endogenous low-molecular-weight compound containing an amino group, carboxyl group, or thiol group, and the like, which can react with various Y1 groups, under conditions similar to those mentioned above, various Y2 groups can be introduced into the starting material.

When (C) is used as the starting material, for example, a compound containing an immunoresponsive hydrophobic group having a reactive group that easily reacts with an amino group is mixed under neutral to basic (pH 7 to 11) conditions at 4 to 80° C., and reacted for 1 min to 24 hr. The subsequent reaction is the same as that when (B) is used as a starting material.

The objective compounds (A)-(C), after chemical reactions, can be separated, collected, and purified by chromatography and the like. The collected solution is volatilized by a lyophilization treatment, evaporation treatment, and the like to obtain the objective compound. When the objective compound is obtained, an oxidation reaction may proceed to form a disulfide bond, whereby the thiol group may disappear. Therefore, a reduction treatment can be performed using dithiothreitol (DTT) and the like at room temperature for 30 to 360 min.

When a high-molecular-weight-imparting group or a labeling compound modifying group is added, for example, the above-mentioned compound can be dissolved in a neutral to basic (pH 7 to 11) buffer containing EDTA, and reacted with a solution containing a polymeric compound or a labeling compound (both including compounds chemically modified with a crosslinking agent) at 4 to 60° C. for 5 to 240 min. The polymeric compound can be the above-mentioned high-molecular-weight-imparting group (carrier protein binding group, synthetic polymer binding group etc.), and can be a protein or polymer having a molecular weight of 10000 or more. The labeling compound can be the above-mentioned labeling compound modifying group. The crosslinking agent can have an active group capable of binding to a thiol group and an amino group. After completion of the reaction, a compound including the high-molecular-weight-imparting group or the labeling compound modifying group (including via the crosslinking agent) bound to a thiol group can be purified by ultrafiltration (molecular weight size 10000 cut-off) or gel filtration chromatography and the like.

2. Method of Producing an Antibody which is Able to Recognize an Endogenous Low-Molecular-Weight Compound A method is described for producing an antibody which is able to recognize an endogenous low-molecular-weight compound, which recognizes a sulfur-containing amino acid derivative having a high-molecular-weight-imparting group and an antigen containing an endogenous low-molecular-weight compound as.

i. Production of Antigen

For the production of an antibody capable of recognizing an endogenous low-molecular-weight compound, an antigen (immunogen) of the antibody needs to be produced. As the antigen, compound (II) can be mainly used, which can be produced by the aforementioned method or as in the below-mentioned Examples.

An antibody obtained using the antigen is not particularly limited as long as it can recognize the endogenous low-molecular-weight compound, and particularly can be one recognizing a part of the surface molecule of the steric structure of the antigen, and more particularly can be one recognizing the part of the immunoresponsive hydrophobic group and endogenous low-molecular-weight compound in the sulfur-containing amino acid derivative. The obtained antibody may be either a monoclonal antibody or a polyclonal antibody. As a polyclonal antibody, various kinds of antibodies such as an antibody recognizing a part of each of a hapten and a protein can be used in addition to an antibody recognizing the objective hapten moiety. As a monoclonal antibody, one superior in selectivity, sensitivity and reproducibility for recognizing a hapten can be used. These monoclonal antibodies and polyclonal antibodies can be produced, for example, as follows without particular limitation.

(b) Production Method for a Monoclonal Antibody

The above-mentioned antigen can be used by itself or together with a diluent or adjuvant, and can be administered to an animal at a site capable of antibody production. As the diluent, water, saline, phosphate buffer and the like can be used. As an adjuvant to increase antibody producibility, Freund's complete adjuvant, Freund's incomplete adjuvant and the like can be used. Administration is generally performed once every 1 to 6 weeks, and 2 to 10 times in total. Examples of the animals which can be used include mouse, guinea pig, rat, goat, monkey, Macaca mulatta, dog, rabbit, bovine, chicken, cat, hamster, sheep, swine, camel and the like, and mouse and rat are particular examples.

For example, an animal immunized with an antigen, particularly, an individual confirmed to have an antibody titer, is selected, the spleen or lymph node is extracted 2 to 5 days after the final immunization, and the cells contained therein are fused with the myeloma cells of homogeneous or heterogeneous animal to prepare a hybridoma. The fusion operation can be performed according to a known method, for example, the method of Köhler and Milstein [Nature, 256:495 (1975)]. Examples of the fusion promoter include polyethylene glycol (PEG), Hemagglutinating Virus of Japan and the like, with preference given to PEG.

Examples of the myeloma cell include NS-1, P3, P3U1, SP2/0, AP-1, MPC-11 and the like, and P3 can be used. A ratio of the number of cells to be used (spleen cells) to the number of myeloma cells is 1:1 to 20:1, PEG (preferably PEG1000-PEG6000), and can be added at a concentration of 10 to 80%, and the mixture is incubated at 20 to 40° C., or 30 to 37° C., for 1 to 20 min to efficiently perform cell fusion.

The hybridoma can be cultured in, for example, a medium for animal cells added with HAT (hypoxanthine, aminopterine, thymidine). Examples of the medium include RPMI1640 medium containing 1 to 20%, or 10 to 20%, fetal bovine serum, GIT medium (manufactured by Wako Pure Chemical Industries, Ltd.) containing 1 to 10% fetal bovine serum, serum-free medium for hybridoma culture (SFM-101, manufactured by NISSUI PHARMACEUTICAL CO., LTD), and the like. The culture temperature is generally 20 to 40° C., or about 37° C. The culture time is generally 5 days to 3 weeks, or 1 week to 2 weeks. Culture can be generally performed in 5% carbon dioxide.

A hybridoma that produces a monoclonal antibody can be screened for by measuring the antibody titer of a culture supernatant by a known method per se. For example, it can be screened for by a method including adding a hybridoma culture supernatant to a solid phase (e.g., microplate) having an antigen or hapten adsorbed thereon, adding an anti-immunoglobulin antibody labeled with a radioactive substance, an enzyme etc. (when the cell used for cell fusion is a cell of mouse, an anti-mouse immunoglobulin antibody is used) or a given protein (protein A, protein G, protein L, protein A/G etc.), and detecting or quantifying a monoclonal antibody bound to the solid phase; a method including adding a hybridoma culture supernatant to a solid phase having an anti-immunoglobulin antibody or protein A and the like adsorbed thereon, adding an antigen labeled with a radioactive substance, an enzyme etc., and detecting or quantifying a monoclonal antibody bound to the solid phase; and the like.

A monoclonal antibody can be obtained from the culture supernatant of the screened hybridoma. In addition, a monoclonal antibody can also be obtained from ascites of an animal by using the hybridoma. For example, when ascites of a mouse is obtained, generally, the hybridoma (e.g., $10^6$ or above) is intraperitoneally transplanted into a mouse (e.g., BALB/c mouse etc.) administered in advance with a substance having an immunosuppressive action such as pristine (2,6,10,14-tetramethylpentadecane) and the like, and ascites which has accumulated in about 1 to 3 weeks can be collected.

A monoclonal antibody can be purified from a culture supernatant of hybridoma or ascites according to a method known per se, for example, separation and purification methods of immunoglobulin, for example, salting out method, alcohol precipitation method, isoelectric precipitation method, electrophoresis method, adsorption and desorption method by an ion exchanger (e.g., DEAE etc.), ultracentrifugation method, gel filtration method, antigen binding solid phase, or a specific purification method including collecting an antibody alone by an active adsorbent such as protein A, protein G, protein L and the like, dissociating a bond to give an antibody.

As one example of the method for producing a monoclonal antibody, for example, a production method including the following steps can be mentioned.

[a] a step of immunizing an animal with an antigen of the above-mentioned compound (II) corresponding to the measurement target endogenous low-molecular-weight compound,

[b] a step of immobilizing a hapten of the above-mentioned formula (I) corresponding to the measurement target endogenous low-molecular-weight compound on a plate to prepare a plate for antibody titer evaluation,

[c] a step of collecting serum from the animal subjected to immunization in step [a], adding the serum to the above-mentioned plate for antibody titer evaluation and measuring the antigen-antibody reaction,

[d] a step of collecting cells from an animal that showed positive in the reaction results of step [c], mixing the cells with myeloma cells to allow cell fusion to prepare hybridomas,

[e] a step of screening for a hybridoma that produces an antibody recognizing hapten of the above-mentioned formula (I) from the hybridomas obtained in step [d],

[f] a step of cloning the hybridoma selected in step [e].

In the above-mentioned step [e], the screening can be performed using the plate for antibody titer evaluation prepared in step [b], and a hybridoma with high antibody producibility can be selected by the screening. Using the selected hybridoma, a desired monoclonal antibody can be obtained from a culture supernatant of hybridoma or ascites of an animal, as mentioned above.

In the present invention, a production method of a monoclonal antibody including the following steps in addition to the above-mentioned steps [a]-[f] is one example:

[g] a step of reacting a hapten of the above-mentioned formula (I) corresponding to a non-measurement target endogenous low-molecular-weight compound with the obtained 2 or more kinds of monoclonal antibodies,

[h] a step of selecting a monoclonal antibody with negative reaction results in step [g].

In the above-mentioned step [g], the selection level of monoclonal antibody can be adjusted by using, as a non-measurement target endogenous low-molecular-weight compound, a compound different in the functional group and structure from the measurement target endogenous low-molecular-weight compound. When a compound more similar to the measurement target endogenous low-molecular-weight compound in the functional group and structure is used, a monoclonal antibody having higher antigen recognition specificity can be selected. For example, when the measurement target endogenous low-molecular-weight compound is glycine, a monoclonal antibody having higher antigen recognition specificity can be selected by using alanine rather than phenylalanine as a non-measurement target endogenous low-molecular-weight compound. A monoclonal antibody having higher antigen recognition specificity by selecting a suitable non-measurement target endogenous low-molecular-weight compound to be used is one particular example. Depending on the conditions of use, moreover, a monoclonal antibody having adjusted antigen recognition specificity can also be employed.

As the monoclonal antibody, when the measurement target is glycine, a monoclonal antibody produced by hybridoma deposited as FERM P-21947 can be used. For example, when the measurement target is phenylalanine, a monoclonal antibody produced by hybridoma deposited as FERM P-21948 can be used. These hybridomas were converted to international deposits and accorded deposit Nos. FERM ABP-11384 and FERM ABP-11385, respectively.

(c) Production Method of Polyclonal Antibody

A polyclonal antibody to the above-mentioned antigen can be produced by a method known to those of ordinary skill in the art. For example, it can be produced by immunizing an animal in the same manner as in the above-mentioned method of producing a monoclonal antibody, collecting a desired antibody containing material from the immunized animal, and separating and purifying the antibody. While the production method of a polyclonal antibody is not particularly limited, the details can be explained as follows.

As an immunization method, an antigen itself or an antigen together with a diluent or adjuvant is/are administered to an animal at a moiety capable of antibody production. As the diluent and adjuvant, those similar to the diluent and adjuvant used for the above-mentioned (b) production method of monoclonal antibody can be mentioned. The administration is generally performed once every 1 to 6 weeks and about 3 to 10 times in total.

A polyclonal antibody is obtained as antiserum by collecting the blood of an immunized animal by the above-mentioned method. The measurement method of the polyclonal antibody titer of the antiserum is the same as the measurement method of antibody titer of the above-mentioned (b) monoclonal antibody. The separation and purification of polyclonal antibody can be performed according to a separation and purification method of immunoglobulin, which is similar to the above-mentioned separation and purification of monoclonal antibody.

3. Measurement Method of Endogenous Low-Molecular-Weight Compound

Using the sulfur-containing amino acid derivative shown in the above-mentioned section 1 and an antibody obtained by the above-mentioned section 2, an endogenous low-molecular-weight compound in a test sample can be measured. That is, a method of measuring an endogenous low-molecular-weight compound including the following steps (A) to (C) is provided:

a step of reacting the derivative of the above-mentioned section 1 with a test sample to form a coupling product of the derivative and an endogenous low-molecular-weight compound present in the test sample, a step of contacting the coupling product obtained in step (A) with the antibody obtained by the above-mentioned section 2, a step of measuring a label of the coupling product bound to the antibody.

For the measurement of an endogenous low-molecular-weight compound, as a sample for the measurement, a coupling product of the sulfur-containing amino acid derivative having a labeling compound modifying group (compound (III) is mainly used) and a measurement target endogenous low-molecular-weight compound can be prepared. The coupling product can be obtained by contacting a test sample containing the endogenous low-molecular-weight compound and the sulfur-containing amino acid derivative. The contact between the two is not particularly limited as long as the conditions permit the endogenous low-molecular-weight compound to form a coupling product with the sulfur-containing amino acid derivative, and they only need to be contacted, that is, reacted at 15 to 40° C. for 1 to 120 min. Examples of the solution which can be used include phosphate buffer, borate buffer and the like, and a known solution can be used according to the measurement means. The sulfur-containing amino acid derivative only needs to be used in an excess amount relative to the endogenous low-molecular-weight compound. For example, a solution is added to a test sample at a concentration of 1 to 100 μmol/mL. While the above-mentioned coupling product includes one wherein the two are not bonded, a coupling product wherein the two are actually bonded is one example.

The test sample which can be used is not particularly limited as long as it contains an endogenous low-molecular-weight compound, or the measurement of the endogenous low-molecular-weight compound is possible. However, since the measurement target is a low-molecular-weight compound in the body of an organism, for which an antibody is difficult to prepare, the sample can be derived from the body. The sample derived from the body may be an animal-derived sample or a plant-derived sample, or may be a processed product (food, drinks etc.) of an animal and/or plant-derived sample. Specific examples of the animal-derived sample include blood, plasma, serum, extravascular fluid, interstitial fluid, cerebrospinal fluid, joint fluid, pleural fluid, lymph fluid, saliva, seminal fluid, tear, urine and the like. Of these, blood, serum, plasma, saliva, seminal fluid, tear and urine are particular examples, blood, serum and plasma are further examples, and plasma and serum are further examples, since they are less invasive for animal. Examples of the plant-derived sample include fruit juice, molasses and the like.

An endogenous low-molecular-weight compound can be measured by applying an antibody obtained by the above-mentioned section 2 to a coupling product of the sulfur-containing amino acid derivative having a labeling compound modifying group and an endogenous low-molecular-weight compound. While the measurement method is not particularly limited, for example, a measurement sample labeled as mentioned above is prepared. Then, the antibody obtained by the above-mentioned 2 is immobilized on a carrier, by which the antibody can recognize a part of the structure of the above-mentioned coupling product (moieties of immunoresponsive hydrophobic group and endogenous low-molecular-weight compound). Then, the coupling product is trapped by the immobilized antibody. Finally, the level of label contained in the trapped coupling product can be determined, and the endogenous low-molecular-weight compound can be measured. As a signal probe, enzyme, radioactive isotope, fluorescent substance, dye, magnetic element and the like are adopted as mentioned above, whereby a signal is detected according to the amount of the measurement target substance. According to this principle, even when the measurement target substance is an endogenous low-molecular-weight compound, an immunoassay by a non-competitive method using a single antibody can be performed, thus enabling a measurement in a shorter time as compared to the competitive method. As a method for measuring an endogenous low-molecular-weight compound by utilizing the obtained antibody, ELISA is one particular example of an immunoassay, in view of the sensitivity, swiftness, accuracy, safety, automation and the like. The measurement method of the above-mentioned endogenous low-molecular-weight compound can be explained in more detail in the following.

1. Immobilization of Antibody

An antibody which recognizes an endogenous low-molecular-weight compound obtained by the above-mentioned section 2 is immobilized on a carrier. As a carrier to be used, synthetic resins such as polystyrene, polyacrylamide, polydivinylbenzene, silicon and the like, glass and the like can be mentioned. Specifically, microtiter plates of 48 well, 96 well, 192 well, 384 well, and the like, which are formed from synthetic resins, are examples. For immobilization of an antibody, for example, a buffer containing an antibody to be immobilized is placed on a carrier, and incubated. Immobilization efficiency can be increased by adsorbing protein A, protein G, protein A/G, protein L, or an antibody recognizing an antibody derived from an animal species immunized to obtain said antibody (for example, when said antibody is obtained from mouse, antimouse antibody derived from rabbit or goat) for coating on a carrier in advance, and adding said antibody. Since an antibody is a molecule containing an amino group, an antibody can be directly immobilized on a carrier by using a carrier on which an N-hydroxysuccinimido activated ester is immobilized. The concentration of the antibody in a buffer is generally 0.01 µg/mL to 100 µg/mL, and a known buffer can be used according to the measurement means.

The antibody to be immobilized may be any as long as it is produced by the method shown in the above-mentioned section 2. It can be an antibody capable of recognizing the structural parts of an immunoresponsive hydrophobic group and an endogenous low-molecular-weight compound in the sulfur-containing amino acid derivative. The antibody may be a monoclonal antibody or a polyclonal antibody, or a part of an antibody having an antigen binding ability such as Fab fragment, $F(ab')_2$ fragment, a polypeptide wherein only a variable portion of said antibody is gene expressed (scFv (single chain variable portion) or hypervariable portion (CDR) etc.).

(b) Blocking

To prevent non-specific adsorption of a protein to a solid phase surface of a carrier, the area of a solid phase surface free of adsorption of an antibody to be immobilized is blocked with a protein and the like irrelevant to the antibody. As an agent for blocking, bovine serum albumin (BSA) or skim milk solution, or commercially available Block Ace (manufactured by DS Pharma Biomedical Co., Ltd.), Applie Block (manufactured by SEIKAGAKU CORPORATION), N101/N102 (manufactured by NOF Corporation) and the like can be used. For blocking, the aforementioned blocking agent can be added to a carrier, and the solution can be incubated at, for example, about 4° C. for 1 hr to one night, and the solid phase can be washed. While the wash is not particularly limited, the same buffer as in the above-mentioned (a) can be used.

(c) Antigen-Antibody Reaction

A sample containing a coupling product of the sulfur-containing amino acid derivative having a labeling compound modifying group and an endogenous low-molecular-weight compound (measurement sample) is added to the solid phase surface treated in the above-mentioned (a) and (b) to perform an antigen-antibody reaction of the antibody immobilized on the carrier and the coupling product. Separately from the measurement sample, a coupling product of the sulfur-containing amino acid derivative having a labeling compound modifying group and an endogenous low-molecular-weight compound can be prepared in advance as a standard sample, various concentrations of the standard sample can be added in parallel to the measurement sample, and an antigen-antibody reaction can be performed in the same manner. All antigen-antibody reactions can be performed generally at 10 to 40° C., or 25 to 37° C., for 1 min to a few hours.

(d) B/F Separation

After performing the antigen-antibody reaction of the above-mentioned (c), the coupling product (B) bound to the immobilized antibody and the unreacted coupling product (F) not bound to the antibody are separated. Separation itself can be performed by washing. While the wash is not particularly limited, the same buffer as in the above-mentioned (a) can be used.

(e) Measurement of Endogenous Low-Molecular-Weight Compound

After the treatment of the above-mentioned (d), the amount of the labeling compound of the coupling product bound to the immobilized antibody is examined, whereby the target endogenous low-molecular-weight compound can be measured. Utilizing various concentrations of the standard sample used in parallel in the above-mentioned (c) for the antigen-antibody reaction, an analytical curve can be drawn in advance. Using the analytical curve, the amount of an endogenous low-molecular-weight compound contained in a test sample can be determined.

When an enzyme is used as a labeling compound, a luminescent substrate solution reactive with the enzyme can be added, and thereafter a given absorbance can be measured, whereby the amount of a labeling compound can be examined. When HorseRadish peroxidase is used as the enzyme, for example, hydrogen peroxide and a luminescent substrate solution containing 3,3',5,5'-tetramethylbenzidine or o-phenylenediamine can be used. Generally, a luminescent substrate solution is added, and the mixture is reacted at room temperature for about 5 to 30 min and sulfuric acid is added to discontinue the enzyme reaction. When 3,3',5,5'-tetramethylbenzidine is used, the absorbance at 450 nm is measured. When o-phenylenediamine is used, the absorbance at 492 nm is measured. To amend background values, it is desirable to also simultaneously measure the absorbance at 630 nm.

When alkaline phosphatase is used as the enzyme, for example, a method including developing color by using p-nitrophenyl phosphate as a substrate, adding a NaOH solution to discontinue the enzyme reaction, and measuring the absorbance at 415 nm can be mentioned. When β-galactosidase is used as the enzyme, for example, a method including developing color by using 4-methylumbelliferyl-β-D-galactopyranoside as a substrate, adding a 0.1M glycine-NaOH buffer (pH 10.3) solution to discontinue the enzyme reaction, and measuring the fluorescence detection intensity at excitation wavelength 360 nm and detection wavelength 450 nm can be mentioned.

When a radioactive substance is used as the labeling compound, the radiation dose thereof can be measured by autoradiography, scintillation counter and the like. When a binding molecule such as biotin or lectin and the like is used instead of a labeling compound, biotin is reacted with labeled avidin or labeled streptavidin, lectin is reacted with labeled saccharide, and the amount of the labeling compound can be examined in the same manner as above. The reaction of a binding molecule can be performed by a method known to those of ordinary skill in the art.

Figure 5:
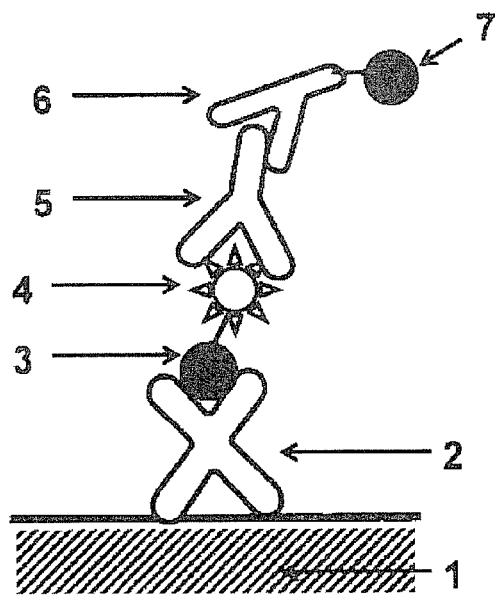
FIG. 5 shows another embodiment of an ELISA measurement of an endogenous low-molecular-weight compound, wherein 1 is a microplate, 2 is avidin or streptavidin, 3 is biotin, 4 is a hapten, 5 is an antihapten antibody, 6 is an antibody recognizing the antihapten antibody, and 7 is a labeling compound.

As another embodiment for measuring an endogenous low-molecular-weight compound, the constitution shown in FIG. 5 can also be used. Here, the objective endogenous low-molecular-weight compound can be measured by using the sulfur-containing amino acid derivative of the above-mentioned 1, which is free of a labeling compound modifying group. To be specific, a sample containing a coupling product of a sulfur-containing amino acid derivative bound to biotin and the like and an endogenous low-molecular-weight compound is added to a plate having avidin or streptavidin and the like immobilized thereon, the coupling product is immobilized on the plate via a binding molecule such as avidin or streptavidin, and biotin, and the like. Then, an antibody recognizing the coupling product is added and an antigen-antibody reaction is performed under given conditions. Furthermore, a labeled antibody (HRP antimouse IgG antibody etc.) recognizing the antibody is added, and the objective endogenous low-molecular-weight compound can be measured by measuring the amount of the label. In the above-mentioned method, washing can be performed appropriately between respective steps.

As another embodiment for measuring an endogenous low-molecular-weight compound, the following method can be mentioned. Also in this embodiment, the objective endogenous low-molecular-weight compound can be measured by using the sulfur-containing amino acid derivative which is free of a labeling compound modifying group but bound to biotin and the like instead. To be specific, the sulfur-containing amino acid derivative is bound to the measurement target endogenous low-molecular-weight compound, and the antibody obtained in the above-mentioned 2 is contacted in the same container to perform an antigen-antibody reaction. The antigen antibody complex obtained by the reaction is immobilized on a carrier such as plate and the like, and labeled avidin or streptavidin is added thereon. As a result, biotin and the like contained in the immobilized antigen antibody complex traps avidin or streptavidin, and the objective endogenous low-molecular-weight compound can be measured by measuring the amount of the label bound to the trapped avidin and the like. Also in the above-mentioned embodiment, washing between the respective steps can be appropriately performed, and a blocking treatment can also be performed for immobilization as appropriate.

EXAMPLES

The present invention is explained in detail by referring to the following non-limiting Examples.

1. Preparation of Immunogen

As an antigen (immunogen) for the preparation of an antibody, synthesized hapten bound with a carrier protein via a crosslinking agent was used. In formula (I), an immunoresponsive hydrophobic group present as moiety X was a 9-fluorenylmethyloxycarbonyl (Fmoc) group or a quinolinylaminocarbonyl group; a measurement target antigen (endogenous low-molecular-weight compound) present as moiety Y was glycine (Gly), phenylalanine (Phe) or isoleucine (Ile); a polymeric carrier protein present as moiety Z was bovine serum albumin (BSA), and a crosslinking agent was sulfosuccinimidyl 4-(N-maleimidomethyl)cyclohexane-1-carboxylate (sulfo-SMCC).

Hapten Synthesis Method 1: Fmoc-Cys[H]-Gly

The starting material (Cys-Gly)$_2$ (manufactured by BACHEM) was dissolved in dimethyl sulfoxide (DMSO) to 20 mmol/L. This solution was diluted 10-fold with 50% acetonitrile solution to give a 2 mmol/L (Cys-Gly)$_2$ solution (5 mL). In addition, 9-fluorenylmethyl succinimidyl carbonate (Fmoc-OSu) (manufactured by Wako Pure Chemical Industries, Ltd.) was dissolved in acetonitrile to 0.25 mol/L.

The 2 mmol/L (Cys-Gly)$_2$ solution (5 mL) and the 0.25 mol/L Fmoc-OSu solution (0.5 mL) were mixed, and the mixture was left standing at 55° C. for 30 min. Then, as a reducing agent, (±)dithiothreitol (DTT) (manufactured by Wako Pure Chemical Industries, Ltd.) was dissolved in ion exchanged water to 3 mol/L, and the 3 mol/L DTT solution (1 mL) was added to the above-mentioned reaction solution. The reaction solution was left standing at 55° C. for 2 hr or longer, and the object compound Fmoc-Cys[H]-Gly was separated and collected by HPLC.

As HPLC apparatus, CLASS-VP series manufactured by Shimadzu Corporation was used wherein the column was a reversed-phase column (inner diameter 4.6 mm×length 250 mm, Cadenza, manufactured by Imtakt Corporation). The analysis conditions were mobile phase A: water/acetonitrile (95/5) added with formic acid at 0.1%, mobile phase B: water/acetonitrile (10/90) added with formic acid at 0.1%, flow rate: 1 mL/min, column oven: 40° C., UV detection wavelength: 265 nm, and elution condition: mobile phase B 45% constant (measurement start time 0-10 min), and mobile phase B 45-100% (10-30 min).

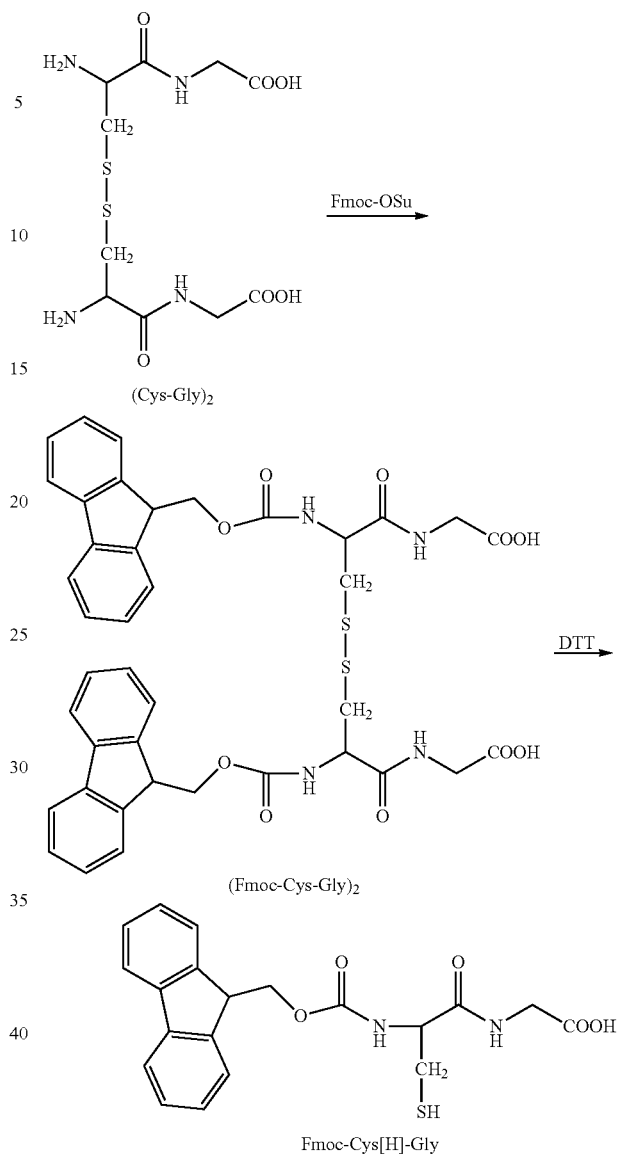

The reaction solution containing Fmoc-Cys[H]-Gly was applied to HPLC, and the peak derived from Fmoc-Cys[H]-Gly was recovered while monitoring the chromatogram. Since the sample injection volume was 400 μl/injection, a recovery operation of the aforementioned reaction solution (total 6.5 mL) was repeated. The recovered fractions were collected in the same container, frozen under liquid nitrogen, and dried in a lyophilizer. The powder obtained by lyophilization weighed 4.79 mg (yield 49%). A portion of the lyophilized compound was re-dissolved, and the rest was preserved at −20° C. until needed. The re-dissolved compound was measured for mass by a mass spectrometer to obtain a mass corresponding to Fmoc-Cys[H]-Gly, which shows that the synthesized hapten was the object compound.

1-2. Hapten Synthesis Method 2: Fmoc-Cys[H]-Phe

The starting material (Cys-Phe)$_2$ (manufactured by BACHEM) was dissolved in dimethyl sulfoxide (DMSO) to 20 mmol/L. The procedures employed after dissolution, the reaction with Fmoc-OSu reagent, the reduction treatment conditions by DTT, and HPLC separation conditions of the object compound Fmoc-Cys[H]-Phe were the same as those for the aforementioned Fmoc-Cys[H]-Gly. The object compound Fmoc-Cys[H]-Phe was recovered and preserved at −20° C. by lyophilization until needed. The re-dissolved compound was measured for mass by a mass spectrometer to obtain a mass corresponding to Fmoc-Cys[H]-Phe, which shows that the synthesized hapten was the object compound.

1-3. Hapten Synthesis Method 3: Fmoc-Cys[H]-Ile

The starting material (Fmoc-Cys)$_2$ (manufactured by BACHEM) was dissolved in DMSO to 200 mmol/L. In addition, a condensing agent N,N'-dicyclohexylcarbodiimide (DCC, manufactured by Tokyo Chemical Industry Co., Ltd.) was separately dissolved in DMSO to 500 mmol/L. Furthermore, N-hydroxysuccinimide (NHS, manufactured by Tokyo Chemical Industry Co., Ltd.) was also separately dissolved in DMSO to 500 mmol/L. The three solutions were mixed (each 1 ml, total 3 mL), and the mixture was reacted with shaking at room temperature for 120 min. A part of the reaction product precipitated with time during the reaction. In addition, Ile was dissolved in a mixture of 0.1N hydrochloric acid/borate buffer (pH 11.0, 50/50) to 200 mmol/L. After completion of the reaction, DMSO (1 mL) was added, and the Ile solution (1 mL) was added in small drop-wise portions. The reaction solution was left to stand at room temperature for 15 min, and 5% acetic acid (0.5 mL) was added. The precipitated compound was subjected to ultra-filtration with a 0.45 μm filter, the filtrate was applied to HPLC, and (Fmoc-Cys-Ile)$_2$ was separated and collected. The HPLC apparatus used was CLASS-VP series manufactured by Shimadzu Corporation, and the column used was a reversed-phase column (inner diameter 4.6 mm×length 250 mm, Cadenza, manufactured by Imtakt Corporation).

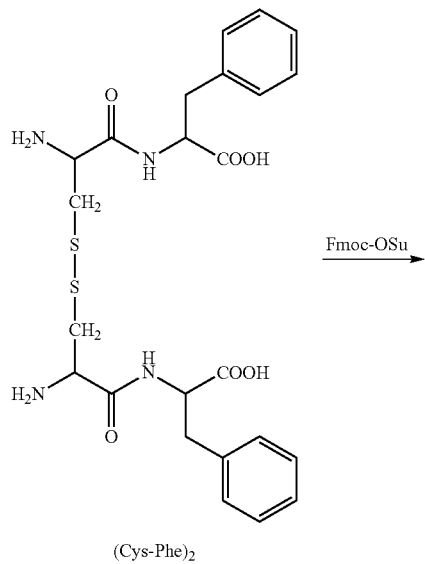

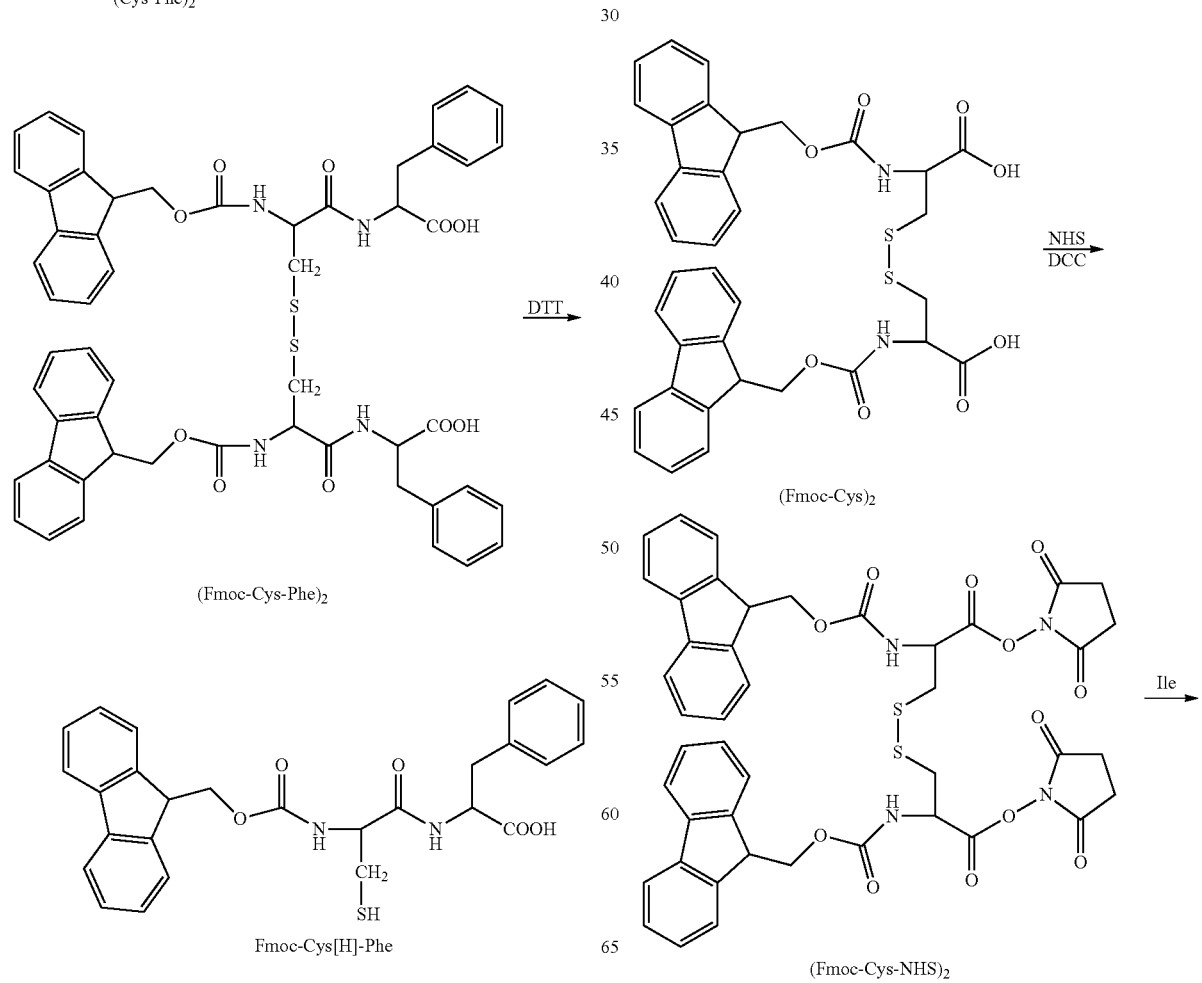

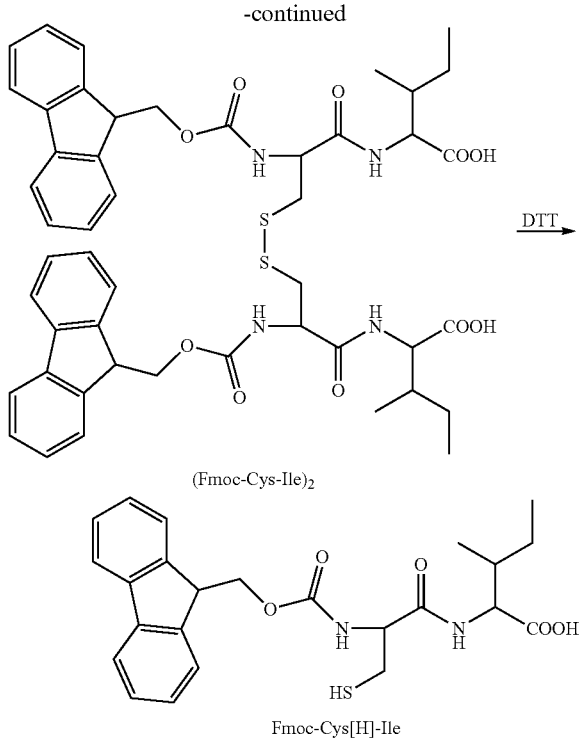

(Fmoc-Cys-Ile)₂

Fmoc-Cys[H]-Ile

The HPLC apparatus and separation column used were the same as those mentioned above, and the analysis conditions of (Fmoc-Cys-Ile)₂ were mobile phase A: water/acetonitrile (95/5) added with formic acid at 0.1%, mobile phase B: water/acetonitrile (10/90) added with formic acid at 0.1%, flow rate: 0.9-1.0 mL/min (measurement start 0-5 min), and 1.0-1.0 mL/min (5-25 min), column oven: 40° C., UV detection wavelength: 265 nm, and elution condition: mobile phase B 72% constant.

The chromatogram obtained by applying the reaction solution containing (Fmoc-Cys-Ile)₂ to HPLC was examined to find that the peak observed around 12 to 14 min from the sample application point was derived from (Fmoc-Cys-Ile/Fmoc-Cys-OH), and the peak observed around 27 min was derived from (Fmoc-Cys-Ile)₂. Both eluted fractions were each recovered while monitoring the chromatogram. Since the sample injection volume was 400 μL/time, a recovery operation of the aforementioned reaction solution (total 5.5 mL) was repeated. The recovered fractions were collected in the same container, frozen under liquid nitrogen, and dried in a lyophilizer. The powder obtained by lyophilization weighed 15.5 mg (yield 13%). The lyophilized compound was re-dissolved in DMSO (1 mL), and a 3 mol/L DTT solution (1.8 mL) was added in small portions. After the completion of addition, the mixture was left standing at 40° C. for 1 hr or longer, and the object compound Fmoc-Cys[H]-Ile was separated and collected by separation by HPLC.

The HPLC apparatus used was CLASS-VP series manufactured by Shimadzu Corporation, and the column used was Cadenza (inner diameter 4.6 mm×length 75 mm, manufactured by Imtakt Corporation). The analysis conditions were mobile phase A: water/acetonitrile (95/5) added with formic acid at 0.1%, mobile phase B: water/acetonitrile (10/90) added with formic acid at 0.1%, flow rate: 1 mL/min, column oven: 40° C., UV detection wavelength: 265 nm, and elution conditions: mobile phase B 40-100% (0-30 min).

The chromatogram obtained by applying the reaction solution containing Fmoc-Cys[H]-Ile to HPLC was measured to find that the peak observed around 10.5 min from the sample application point was derived from Fmoc-Cys[H]-Ile. The eluted fractions were recovered while monitoring the chromatogram. Since the sample injection volume was 400 μL/time, a recovery operation of the aforementioned reaction solution (total 2.6 mL) was repeated. The recovered fractions were collected in the same container, frozen under liquid nitrogen, and dried in a lyophilizer. The powder obtained by lyophilization was 1.8 mg (yield 24%).

1-4. Hapten Synthesis Method 4: AQC-Cys[H]-Phe

The starting material (Cys-Phe)₂ (manufactured by BACHEM) was dissolved in 0.1M hydrochloric acid to 10 mmol/L. In addition, the AccQ•Ultra Derivatization Reagent of an AccQ•Tag Ultra Derivatization Kit (manufactured by Waters) was prepared to 100 mmol/L (AQC reagent) with acetonitrile. The prepared (Cys-Phe)₂ solution (500 μL), an AQC reagent (1000 μL) and 0.1 mol/L borate buffer (1000 μL) were mixed, and the mixture was heated at 55° C. for 20 min. Then, a 2 mol/L aqueous DTT solution (250 μL) was added and the mixture was reacted at 40° C. for 2 hr. Thereafter, 0.2% acetic acid (2.25 mL) was added to discontinue the reaction, and the object compound AQC-Cys[H]-Phe was separated and collected by HPLC. While this hapten was bound to a quinolinylaminocarbonyl group, since it is a group derived from AQC, the above-mentioned name was used.

The HPLC apparatus used was CLASS-VP series manufactured by Shimadzu Corporation, and the separation column used was a reversed-phase column (inner diameter 4.6 mm×length 250 mm, Cadenza, manufactured by Imtakt Corporation). The analysis conditions of AQC-Cys[H]-Phe were mobile phase A: water/acetonitrile (95/5) added with formic acid at 0.1%, mobile phase B: water/acetonitrile (10/90) added with formic acid at 0.1%, flow rate: 1 mL/min, column oven: 40° C., UV detection wavelength: 265 nm, and elution conditions: mobile phase B 15-60% (0-10 min).

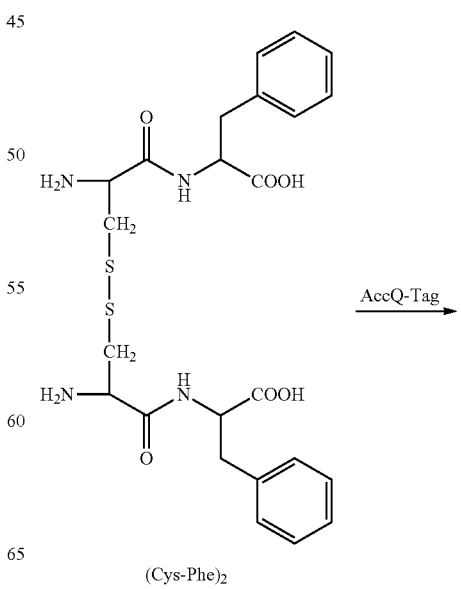

(Cys-Phe)₂

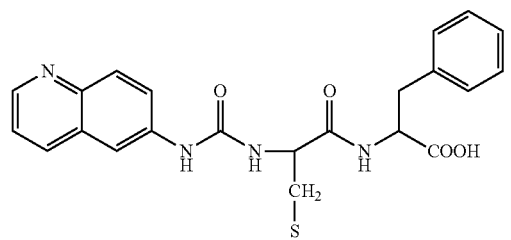

(AQC-Cys-Phe)$_2$

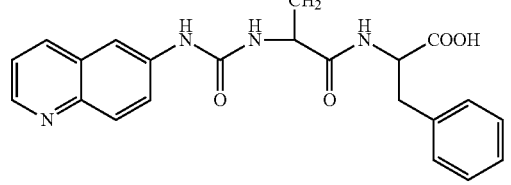

AQC-Cys[H]-Phe 1-5. Hapten Synthesis Method 5: Cys[H]-Phe

The starting material (Cys-Phe)$_2$ (manufactured by BACHEM) was dissolved in 0.1M hydrochloric acid to 10 mmol/L. Then, a 2 mol/L aqueous DTT solution (250 μL) was added and the mixture was reacted at 40° C. for 2 hr. Thereafter, the object compound Cys[H]-Phe was separated and collected by HPLC.

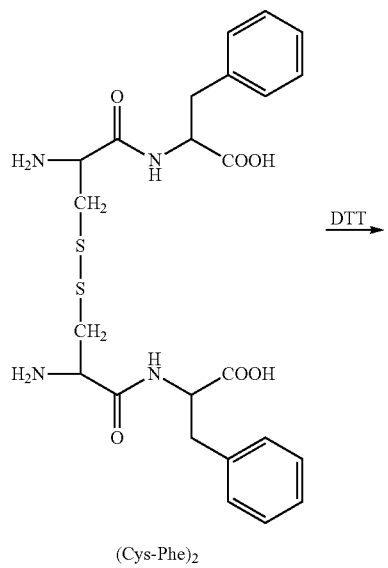

(Cys-Phe)$_2$

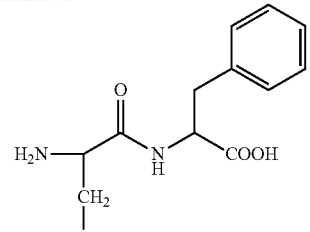

Cys[H]-Phe 1-6. Binding of Hapten and Carrier Protein

To bind BSA and each of the synthesized hapten Fmoc-Cys[H]-Gly, Fmoc-Cys[H]-Phe, Fmoc-Cys[H]-Ile, AQC-Cys[H]-Phe and Cys[H]-Phe, Imject (registered trade mark) Maleimido Activated BSA (manufactured by Pias Corporation) was used. The maleimido-activated BSA is BSA wherein a crosslinking agent Sulfo-SMCC-maleimido group has already been introduced via an amino (ε-NH$_2$) group derived from the Lys residue on the surface of BSA. A maleimido-activated BSA (2 mg) was dissolved in 50 mM phosphate buffer (pH 7.3, containing 0.1-Methylenediamine-N,N,N',N'-tetraacetic acid 4 sodium salt tetrahydrate, manufactured by DOJINDO LABORATORIES, 1 mL). The synthesized various haptens (0.5 mg) were dissolved in 200 μL of dimethyl sulfoxide, and the mixtures were slowly added dropwise to the maleimido-activated BSA solution. After the dropwise addition, the mixtures were left standing at room temperature for 2 hr. After completion of the reaction, they were subjected to ultrafiltration by centrifugation using Amicon (registered trade mark) Ultra-4 (molecular weight 10,000 Da cut-off, manufactured by Millipore). After the centrifugal treatment, 50 mM phosphate buffer (pH 7.3) was repeatedly added about 6-7 times to remove excess EDTA as much as possible. Thereafter, protein was quantified by the Bradford method, and the concentration of each hapten-BSA conjugate was determined to obtain 0.50-0.92 mg/mL.

To confirm the amount of hapten bound to 1 molecule of maleimido-activated BSA, the hapten-BSA conjugate was measured with a mass spectrometer, matrix-assisted laser desorption/ionization method-time-of-flight mass spectrometer (MALDI-TOF MS). FIG. 1 shows MALDI-TOF MS spectra of chemically-unmodified BSA, maleimido-activated BSA, and Fmoc-Cys[H]-Gly/BSA conjugate. The mass difference between chemically-unmodified BSA and maleimido-activated BSA was 8186. Since a molecular weight of 220 increases by introduction of one maleimido activated group into the BSA molecule, it was found that 37 residual maleimido groups on average are introduced per molecule of the maleimido-activated BSA. In addition, a peak of further increased molecular weight was observed in the sample wherein each hapten was bound to maleimido-activated BSA. In the Fmoc-Cys[H]-Gly/BSA conjugate, the mass difference from the maleimido-activated BSA was 10248. Since Fmoc-Cys[H]-Gly has a molecular weight of 386, it was found that 26 residual Fmoc-Cys[H]-Gly on average were introduced per molecule of the maleimido-activated BSA. Furthermore, a similar mass increase was observed when Fmoc-Cys[H]-Phe, Fmoc-Cys[H]-Ile, AQC-Cys[H]-Phe and Cys[H]-Phe were reacted with maleimido-activated BSA, and it was found that not less than 10 residual haptens were respectively introduced per molecule of the maleimido-activated BSA.

2. Production of Antibody

2-1. From Immunization Operation to Antiserum Evaluation

Before immunization, BALB/c mice (female, 4-week-old) were pre-bred for 1 week. The prepared Fmoc-Cys[H]-Gly/BSA conjugate solution (50 μg/100 μL/mouse) was mixed with an equal amount of Freund's complete adjuvant (manufactured by DIFCO) to form an emulsion. This suspension was subcutaneously administered to the back of a sheared mouse at several sites for the first immunization. Two weeks later, as the second immunization treatment, a similar procedure was performed using Freund's incomplete adjuvant (manufactured by DIFCO) instead of the Freund's complete adjuvant. Two weeks later, as the third immunization treatment, a procedure similar to the second immunization treatment was performed. One week from the third immunization treatment, blood was partially drawn from the mouse, and the antibody titer was measured by an enzyme immunoassay (ELISA) to confirm antibody production in the mouse. The next day, the last immunization treatment was performed by a method similar to the second immunization treatment. Three days from the last immunization treatment, the spleen was aseptically isolated from the mouse, and spleen cells were prepared and subjected to cell fusion. A similar treatment was performed for other hapten-BSA conjugates.

2-2. Production of Plate for Antibody Titer Evaluation

Fmoc-Cys[H]-Gly was immobilized on a 96-well microplate of Reacti-Bind (trademark) Maleimide Activated Plates (manufactured by Pias Corporation). Fmoc-Cys[H]-Gly was prepared to 2 μg/mL with 50 mM phosphate buffer (containing 10 mM EDTA), the solution was added by 100 μL to each well of the above-mentioned plate, and the plate was left standing at 4° C. overnight. Then, the inside of the well was washed three times with PBS (containing 0.05% Tween 20). After washing, a 10 μg/mL cysteine solution was added to each well by 200 μL, the plate was left standing at room temperature for 1 hr to allow a quenching treatment of unreacted maleimido group on the plate. Sequentially, the inside of the well was washed three times with PBS (containing 0.05% Tween 20) to give a Fmoc-Cys[H]-Gly solid phased plate. The plate was preserved at 4° C. until needed. A similar treatment was performed for other haptens to produce plates for antibody titer evaluation.

2-3. Antibody Titer Evaluation

The blood partially collected from the immunized mouse was left standing at room temperature for 1 hr or longer, and coagulated blood was triturated with Pasteur pipette etc. and subjected to centrifugation (3000 rpm, 15 min) to give a serum. The obtained serum was serially diluted with 0.1% gelatin (manufactured by Nacalai Tesque)-containing PBS buffer ($10^3$-$10^6$-fold diluted). The serially diluted serum was added by 100 μL to given wells in the above-mentioned plate for antibody titer evaluation, and the plate was left standing at room temperature for 1 hr. Then, the inside of the well was washed three times with PBS (containing 0.05% Tween 20), Peroxidase Conjugated Affinity Purified Anti-Mouse IgG Fc specific antibody (Goat) (manufactured by Jackson Immuno Research) was added, and the plate was left to stand at room temperature for 1 hr. Thereafter, the inside of the well was washed three times with PBS (containing 0.05% Tween 20). The antigen-antibody reaction was confirmed using an OPD solution (0.04% [w/v] o-phenylenediamine-containing 20 mM citrate buffer (pH 5.0) added with 0.018% [v/v] hydrogen peroxide solution immediately before reaction) or a TMB one solution (manufactured by Promega KK.). Various solutions were added to each well by 100 μL, the mixture was allowed to develop color for 10 min, and the chromogenic reaction was discontinued with a 1N sulfuric acid solution. After discontinuation of the chromogenic reaction, the absorbance at wavelength 492 nm was measured for OPD luminescence and the absorbance at wavelength 450 nm was measured for TMB luminescence, each with microplate reader SpectraMax M2e (manufactured by Molecular Devices).

2-4. Cell Fusion

The spleen aseptically isolated from the mouse as mentioned above was triturated in MEM-α medium (manufactured by Gibco) in a cell strainer (manufactured by Falcon). The mouse myeloma cell line P3-Ag-X3 cells were cultured in a sufficient amount in advance, recovered, and the number thereof was counted. Assuming the number of the cells contained in one spleen is $1 \times 10^8$ cells, splenocyte and myeloma cell were mixed such that the number of the cells was splenocyte:myeloma cell=5:1. The culture supernatant was removed by centrifugation, and the cell pellets were triturated. The container of the cell pellets was immersed in a water bath at 37° C., and a PEG1500 (manufactured by Roche Diagnostics K.K.) solution (1 mL) was added by small portions over 1 min while rotating the container to start cell fusion. The mixture was vigorously pipetted for 1 min from 1 min after addition of the PEG solution. Then, a total 4 mL of MEM-α medium was added for 4 min thereafter. Furthermore, 10 mL of MEM-α medium was added for 2 min thereafter. After standing at room temperature for 5 min, the supernatant was removed by centrifugation, and the fused cells were suspended in HAT medium (160 mL, MEM-α medium containing 0.01 mM hypoxanthine, 0.04 μM aminopterine and 1.6 μM thymidine and added with 10% FCS solution). Finally, this suspension was shown in each well of a 96 well microplate by 200 μL, and cultured at 5% $CO_2$, 37° C. Thereafter, a half amount of the medium in each well was removed every 3 days, and fresh HAT medium was added in a half amount. From 10 days after the cell fusion, the medium was exchanged with HT medium (MEM-α medium containing 0.01 mM hypoxanthine and 1.6 μM thymidine and added with 10% FCS solution) in the same manner as with the HAT medium.

2-5. Screening

After the cell fusion, screening was performed to evaluate whether the objective antibody had been secreted from the grown hybridoma. The culture supernatant on day 10 to day 16 after the cell fusion was collected by 50 μL from each well, the supernatant was added to the above-mentioned plate for antibody titer evaluation, and the plate was left to stand for 1 hr. The inside of the well was washed three times with PBS (containing 0.05% Tween 20), Peroxidase Conjugated Affinity Purified Anti-Mouse IgG Fc specific antibody (Goat) (manufactured by Jackson Immuno Research) was added, and the plate was left standing at room temperature for 1 hr. Thereafter, the inside of the well was washed three times with PBS (containing 0.05% Tween 20). The antigen-antibody reaction was evaluated by adding 100 μL of an OPD solution (20 mM citrate buffer containing 0.04% [w/v] o-phenylenediamine (pH 5.0); 0.018% [v/v] hydrogen peroxide was added immediately before reaction) to each well and measuring the absorbance (measurement wavelength 492 nm). The well with an absorbance of 0.5 or more was evaluated as a positive well, the cell culture medium inside the positive well was transferred to a different 96-well microplate, and the culture was continued. Since the well evaluated to be positive by the primary screening also contained pseudo-positive well, the culture was continued for 1 week, the culture supernatant was subjected to the second screening by a similar operation, and the well that showed an absorbance of 3.0 or more was evaluated as a positive well.

2-6. Cloning

Monocloning of the cell was performed by the following limiting dilution method. After the secondary screening, the cell suspension in the well evaluated as positive was serially diluted 100-fold, 1000-fold and 10000-fold with a complete medium (BM medium) containing 10% [v/v] BM condemned H1 (manufactured by Roche). Each diluted cell suspension was respectively added to 32 wells of one 96-well microplate, and the culture was continued. In culture, a half amount of the medium was exchanged with BM medium every 6 days. After 10-15 days from the start of the culture, colony was observed under a microscope. The supernatant sample of a well observed to contain single colony therein was examined for the presence or absence of antibody activity. When the culture supernatant containing a monocloned hybridoma was evaluated as positive, it was subjected again to cloning by the limiting dilution method (recloning). After the recloning, the well observed to contain a single colony under a microscope was determined in the same manner, and the culture supernatant was confirmed as positive, then a monoclonal antibody producing hybridoma was obtained. The obtained hybridoma was deposited on Apr. 1, 2010 at the National Institute of Advanced Industrial Science and Technology International Patent Organism Depositary (1-1-1 Higashi, Tsukuba, Ibaraki, AIST Tsukuba Central 6), the hybridoma that produces a monoclonal antibody to Fmoc-Cys-Gly was accorded deposit No. FERM P-21947, and the hybridoma that produces a monoclonal antibody to Fmoc-Cys-Phe was accorded deposit No. FERM P-21948. All these hybridomas were converted to an international deposit in the institute, the hybridoma that produces a monoclonal antibody to Fmoc-Cys-Gly was accorded deposit No. FERM ASP-11384, and the hybridoma that produces a monoclonal antibody to Fmoc-Cys-Phe was accorded deposit No. FERM ABP-11385 (Date of notice of deposit: May 16, 2011).

2-7. Obtaining Monoclonal Antibodies to Various Immunogens

The following Table 1 shows the results of the number of positive wells or hybridoma strains in the step of producing a monoclonal antibody to each immunogen. 5 to 10 monoclonal antibody producing cell lines for Fmoc-Cys-Gly, Fmoc-Cys-Phe, Fmoc-Cys-Ile, and AQC-Cys-Phe were finally established. On the other hand, in the design using Cys-Phe as an immunogen, the number of wells evaluated as positive by the primary screening was small, and the cells dropped out with the progress of the antibody-producing step. From these results, it was concluded that the immunological response was enhanced by the introduction of a structure having Fmoc or AQC structure, which is absent in the body, into the Cys amino group moiety, and the antibody could be easily obtained.

TABLE 1

| monoclonal antibody production step | operation contents | immunogen | | | | |
|---|---|---|---|---|---|---|
| | | Fmoc-Cys-Gly | Fmoc-Cys-Ile | Fmoc-Cys-Phe | AQC-Cys-Phe | Cys-Phe |
| step 1 | primary screening (number of positive wells) | 32 | 136 | 96 | 96 | 9 |
| step 2 | secondary screening (number of positive wells) | 10 | 10 | 14 | 12 | not measured |
| step 3 | cloning (number of cell lines) | 8 | 8 | 11 | 11 | 3 |
| step 4 | recloning (number of cell lines) | 8 | 8 | 10 | 9 | 0 |
| step 5 | Final positive confirmed | 8 | 8 | 10 | 6 | 0 |
| step 6 | number of established antibody producing cell lines | 8 | 8 | 10 | 5 | 0 |

2-8. Large Scale Production and Purification of Monoclonal Antibody

Since a sufficient evaluation cannot be performed with an antibody in the amount derived from the culture supernatant, the antibody was produced in larger amounts using ascites. An established hybridoma strain was cultured in a complete medium and suspended in MEM-α medium at $1 \times 10^7$ strains/mL concentration. The suspension was intraperitoneally administered to a BALE/c mouse which had been treated with pristine (0.5 mL/mouse) in advance 7 days before. After 7-14 days, the ascites were collected from the mouse, and the cells were removed by centrifugation.

The obtained ascites were purified with a Protein G column (manufactured by GE Healthcare). The Protein G column was equilibrated with 20 mM phosphate buffer (pH 7.0), the ascites were diluted 10-fold with 20 mM phosphate buffer (pH 7.0) and added to the Protein G column to allow adsorption of antibody component (immunoglobulin G) in the ascites. The contaminant components remaining in the column were removed by washing with 20 mM phosphate buffer (pH 7.0) solution, and the antibody component was eluted with glycine buffer. The eluted antibody component in the eluate was immediately neutralized with 1M Tris buffer (pH 9.0). The purified antibody solution was cryopreserved at −20° C. until needed.

3. Preparation of Derivatization Reagent 3-1. Preparation of Derivatization Reagent: Biotin-[Fmoc-Cys]

(Fmoc-Cys)$_2$ (manufactured by BACHEM) was dissolved in acetonitrile to 20 μM, 3 mol/L dithiothreitol was added and the mixture was left standing at 40° C. for 1 hr. Fmoc-Cys[H] fraction was separated with an HPLC apparatus and lyophilized. After lyophilization, the fraction was dissolved in 50 mM phosphate buffer (pH 6.0) to give an Fmoc-Cys[H] solution. Maleimido-PEG2-Biotin (manufactured by PIERCE) was dissolved in 50 mM phosphate buffer (pH 7.3) containing 0.1% EDTA, then mixed with a Fmoc-Cys[H] solution, and the mixture was left to stand at room temperature for 2 hr. The reaction mixture was applied to HPLC, and a biotin-[Fmoc-Cys] fraction was collected by separation and lyophilized.

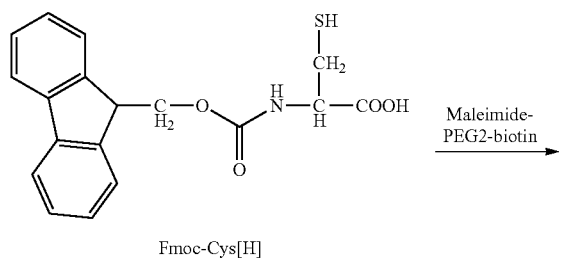

Fmoc-Cys[H]

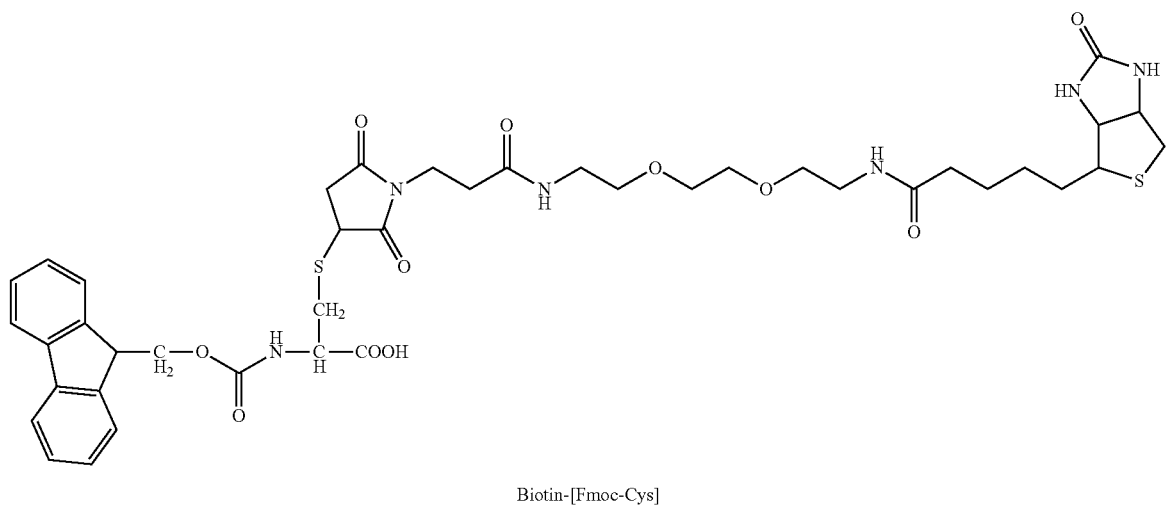

Biotin-[Fmoc-Cys]

3-2. Preparation of Derivatization Reagent: Biotin-[Fmoc-Cys-NHS]

N,N-Dicyclohexylcarbodiimide (DCC) and N-hydroxysuccinylimide (NHS) were each dissolved in acetonitrile to 0.1 mol/L. The biotin-[Fmoc-Cys] lyophilized product prepared above was weighted (1 μg) and dissolved in acetonitrile (56 μL). A 0.1 mol/L DCC solution (12 μL) and a 0.1 mol/L NHS solution (12 μL) were added to this solution, and the mixture was left to stand at room temperature for 2 hr.

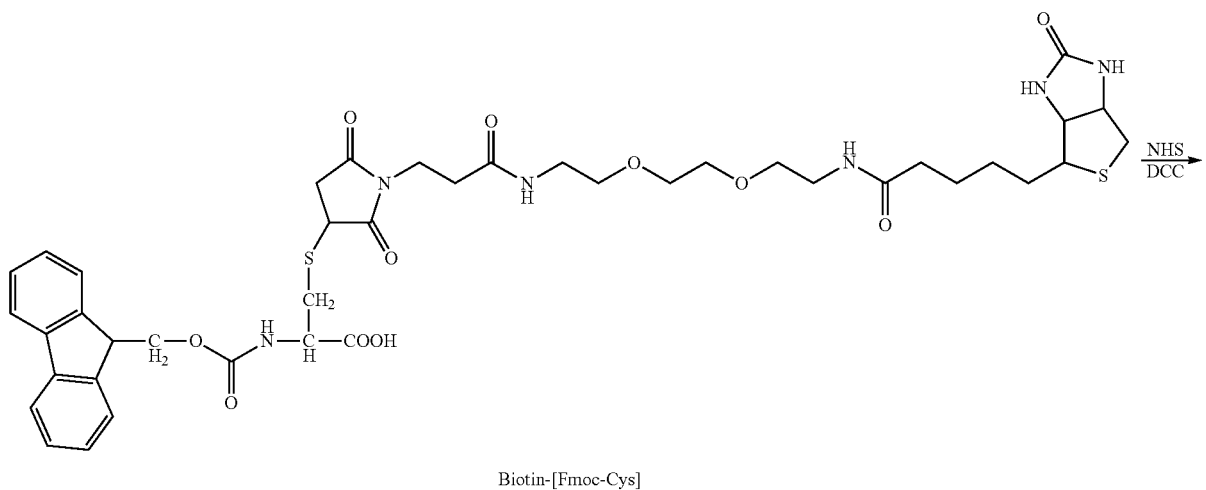

Biotin-[Fmoc-Cys]

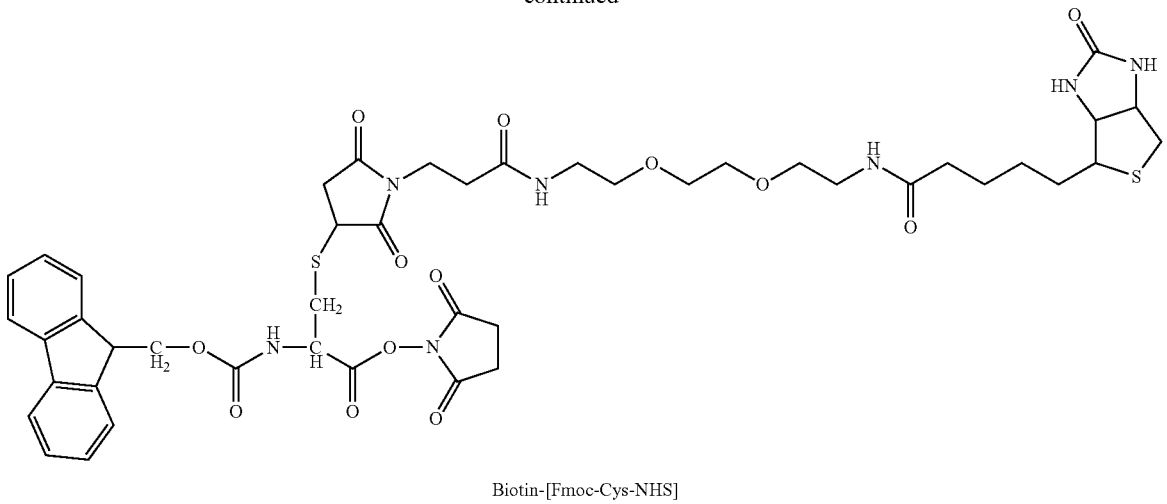

Biotin-[Fmoc-Cys-NHS]

3-3. Derivatization Reaction: Amino Acid Derivatization by Biotin-[Fmoc-Cys-NHS]

An amino acid solution and a 0.1M borate buffer (pH 9.0) were added to the prepared biotin-[Fmoc-Cys-NHS], and the mixture was left to stand at room temperature for 15 min. Thereafter, 0.2% acetic acid was added to discontinue the derivatization reaction. The reaction mixture was preserved at 4° C. until measurement.

4. Antibody Evaluation: ELISA

Figure 2:
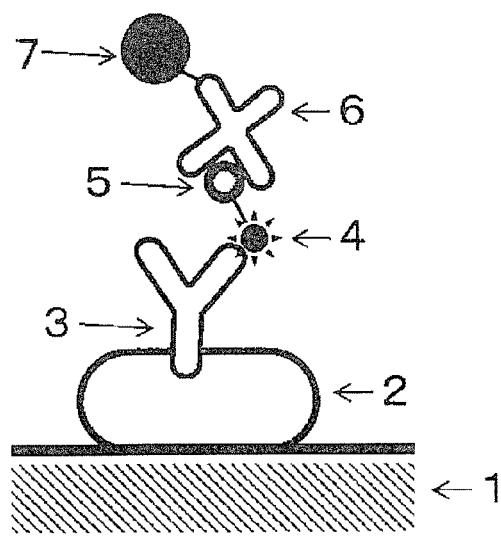
FIG. 2 shows one embodiment of an ELISA measurement of an endogenous low-molecular-weight compound, wherein 1 is a microplate, 2 is a protein A/G, 3 is an antihapten antibody, 4 is a hapten, 5 is biotin, 6 is avidin or streptavidin, and 7 is HorseRadish peroxidase (HRP).

The measurement principle using ELISA is shown in FIG. 2. A solution of an antibody recognizing Fmoc-Cys-Gly was diluted to 0.1 μg/mL with 50 mM phosphate buffer (pH 7.3, PBS) containing 0.9% sodium chloride. 100 μl, of this solution was added to each well of Reacti-Bind (Trademark) Protein A/G Coated Plate (manufactured by Thermo Scientific), and the plate was left to stand at room temperature for 2 hr. Then, the inside of the well was washed three times with 0.05% Tween 20-containing phosphate buffer (PBST). A biotin-[Fmoc-Cys-Gly] compound was serially diluted with 0.1% gelatin containing PBS solution (GPB), the diluted solution was added by 100 μL to each well, and an antigen-antibody reaction was performed. After standing at room temperature for 60 min, the inside of the well was washed three times with PBST solution. After washing, 100 μL of 1 μg/ml HRP-labeled streptavidin conjugate solution was added to each well, and the plate was left to stand at room temperature for 60 min. The inside of the well was further washed three times with PBST, 100 μL of an OPD solution (25 mM citric acid/50 mM disodium hydrogen phosphate (pH 5.0) solution (10 mL) containing o-phenylenediamine (4 mg) and hydrogen peroxide (6 μL)) was added to each well as an HRP substrate solution to perform a luminescence reaction. After 10 min from the start of the reaction, 1M sulfuric acid was added by 100 μL to each well as a reaction quenching liquid, and the absorbance of each well was measured at measurement wavelength (492 nm).

Using a biotin-[Fmoc-Cys-Gly] standard solution, which is an antigen standard solution, it was confirmed whether or not the ELISA principle of FIG. 2 could be established for the anti-Fmoc-Cys-Gly antibody obtained as mentioned above. As a result, a dose-response curve, wherein the absorbance also increases along with the concentration of the antigen standard solution, was obtained (FIG. 3A). Therefrom it was confirmed that the ELISA principle was established for the anti-Fmoc-Cys-Gly antibody.

Then, to evaluate the specificity of the anti-Fmoc-Cys-Gly antibody, the responsiveness to each amino acid other than Gly was evaluated. As each amino acid, glycine, sarcosine, alanine, β-alanine, γ-aminobutyric acid (GABA), serine, proline, valine, taurine, threonine, valine, leucine, isoleucine, asparagine, aspartic acid, glutamic acid, methionine, histidine, phenylalanine, arginine and tryptophan were applied. Biotin-[Fmoc-Cys-NHS], which is an amino acid derivatization reagent, and an amino acid (1 to 1000 μmol/L) were reacted at room temperature for 15 min, and 0.2% acetic acid was added to discontinue the reaction. The derivatization reaction mixture was diluted 1000-fold with a PBS solution containing 0.1% gelatin and used as a sample for ELISA measurement. As a plate for ELISA measurement, a Protein A/G Coated plate (manufactured by Thermo Scientific) was used, and an anti-Fmoc-Cys-Gly antibody solution (concentration 0.1 μg/mL) was added by 100 μL to each well. The plate was left standing at room temperature for 2 hr to immobilize the antibody. Then, the inside of each well was washed three times with PBST, the sample for ELISA measurement was added by 100 μL to each well, and the plate was left to stand at room temperature for 1 hr. Then, each well was washed, a 1 μg/mL streptavidin-HRP conjugate (manufactured by Jackson Immuno Research) solution (diluted 1000-fold with GPB solution containing 5%[v/v] Applie Block (manufactured by SEIKAGAKU CORPORATION)) was added by 100 μL to each well, and the plate was left to stand at room temperature for 1 hr. Thereafter, each well was washed, and a color developing reaction was performed using an OPD solution.

Figure 3:
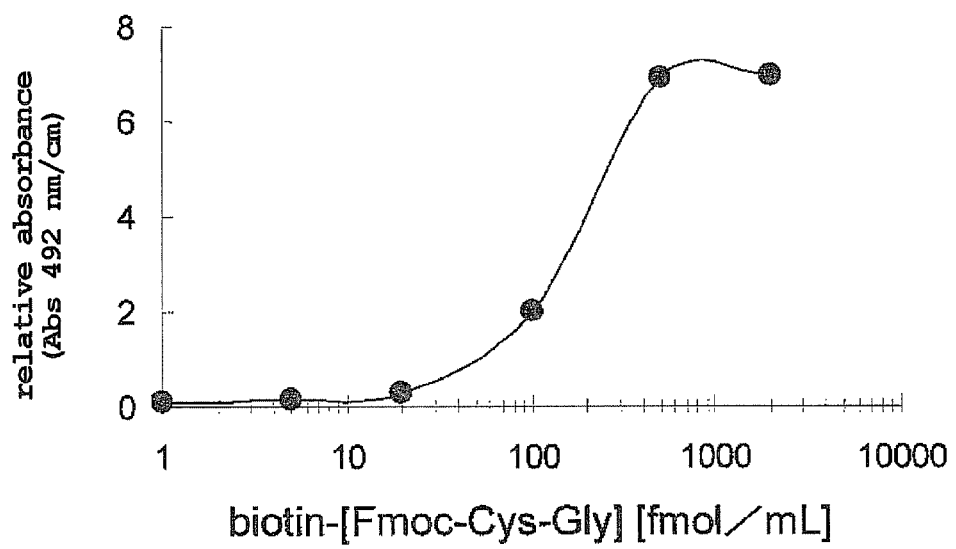
FIG. 3 shows the results of the reactivity of anti-Fmoc-Cys-Gly antibody, wherein A is a dose-response curve showing the reactivity to biotin-[Fmoc-Cys-Gly] standard solution. In the graph, the horizontal axis shows the concentration of the standard solution, and the vertical axis shows the relative absorbance at measurement wavelength 492 nm. B is a graph showing the cross-reactivity of anti-Fmoc-Cys-Gly antibody to various amino acid standard solutions. In the graph, the horizontal axis shows the concentrations of the various amino acid standard solutions and the vertical axis shows the relative absorbance at measurement wavelength 492 nm.
Figure 3:
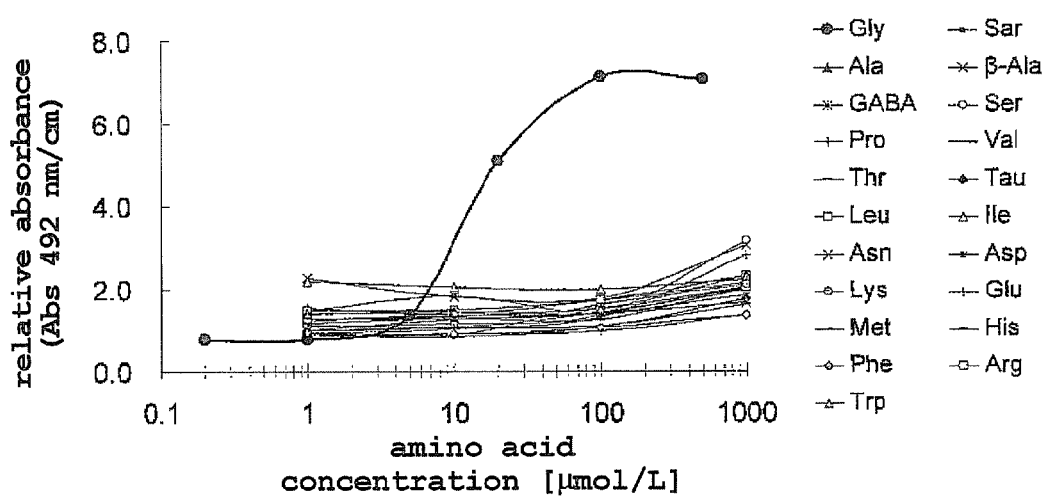

The absorbance corresponding to each amino acid concentration was plotted and shown in FIG. 3 B. Therefrom it was shown that an anti-Fmoc-Cys-Gly antibody selectively responds only to Gly and scarcely shows a response to other amino acids.

The anti-Fmoc-Cys-Phe antibody and anti-Fmoc-Cys-Ile antibody produced in the same manner were also examined for cross reactivity with amino acids other than Phe and Ile. As a result, when the reactivity of the anti-Fmoc-Cys-Phe antibody with Phe was 100%, the cross reactivity with other amino acids were 11% for Tyr, 10% for Leu and 0.1% or less for other amino acids. In the case of the anti-Fmoc-Cys-Ile antibody, when the reactivity with Ile was 100%, the cross reactivity with Leu was 16%, that with Phe was 13%, and those with other amino acids were 1% or less. From these results, it was shown that the anti-Fmoc-Cys-Phe antibody and anti-Fmoc-Cys-Ile antibody can be utilized as tools for selectively detecting the measurement target.

5. Quantification of Amino Acid Using Real Sample 5-1. Quantification of Glycine (Gly)

As real samples, Japanese sake (Masurao, manufactured by KANO SYUZOU CO., LTD.), fetal bovine serum (FCS, Fetal Bovine Serum, manufactured by Invitrogen) and rat plasma sample (SD, female, 20-week-old, manufactured by CHARLES RIVER LABORATORIES JAPAN, INC.) were used, and measurement evaluation of Gly in the samples was performed using the anti-Fmoc-Cys-Gly antibody and an amino acid derivatization reagent. The evaluation was performed by comparing the Gly measurement value determined by ELISA based on the principle of FIG. 2 and the Gly measurement value obtained with high performance liquid chromatography-mass spectrometer (LC-MS; high performance liquid chromatography apparatus; 1100 series (manufactured by Agilent Technologies), mass spectrometer; API3000 (manufactured by Applied Biosystems)).

The protein in the real sample was precipitated by mixing the sample and acetonitrile at 1:1. They were mixed by vortex-stirring for about 15 to 30 sec, and the protein was precipitated by a centrifugation operation. The supernatant after treatment was diluted 1- to 100-fold with PBS solution, and subjected to a derivatization reaction with a biotin-[Fmoc-Cys-NHS] reagent. For the derivatization reaction, acetonitrile (11 µL), 0.1M borate buffer (pH 9, 4 µl), the above-mentioned protein sample (4 µL) and the derivatization reagent biotin-[Fmoc-Cys-NHS] (1 µl) were mixed. They were mixed by vortex-stirring for about 15 to 30 sec, and left standing at room temperature for 15 min. Then, 0.2% acetic acid solution (20 µl) was added to discontinue the derivatization reaction.

Separately, a Gly standard solution to be used for analytical curve was serially diluted with PBS to fall within the concentration range of 0.1 to 1000 µM, and the Gly standard solution at each concentration and acetonitrile were mixed at 1:1. The Gly standard solution after mixing with acetonitrile was subjected to a derivatization reaction with a biotin-[Fmoc-Cys-NHS] reagent. For the derivatization reaction, acetonitrile (11 µL), 0.1M borate buffer (pH 9, 4 µL), the above-mentioned acetonitrile-mixed Gly standard solution (4 µL) and the derivatization reagent biotin-[Fmoc-Cys-NHS] (1 µL) were mixed. They were mixed by vortex-stirring for about 15 to 30 sec, and left standing at room temperature for 15 min. Then, 0.2% acetic acid solution (20 µL) was added to discontinue the derivatization reaction. The real sample and Gly standard solution after the derivatization reaction were diluted 2000-fold with 0.1% gelatin-containing PBS solution and subjected to ELISA measurement.

The Gly quantification by ELISA measurement was performed according to the following procedures. First, 100 µL of an anti-Fmoc-Cys-Gly antibody (concentration 0.1 µg/mL) was added to each well of a Protein A/G coating plate, and the plate was left to stand at room temperature for 2 hr. Then, the inside of the well was washed three times with PBST solution to give an anti-Fmoc-Cys-Gly antibody solid-phased plate. To each well of the plate was added a real sample or a Gly standard solution (each 100 µL) after derivatization reaction and dilution treatment, and the plate was left to stand at room temperature for 1 hr. During this operation, all wells were tightly sealed with a plate seal. Then, the inside of the well was washed three times with PBST solution, and 100 µL of a streptavidin-HRP conjugate solution diluted to a concentration of 1 µg/mL with an Applie Block/GPB (5/95) mixture was added to each well. After standing at room temperature for 1 hr (during which all wells were tightly sealed with plate seal), the inside of the well was washed three times with PBST solution. Thereafter, each well was washed, and a color developing reaction was performed using an OPD solution.

Figure 4:
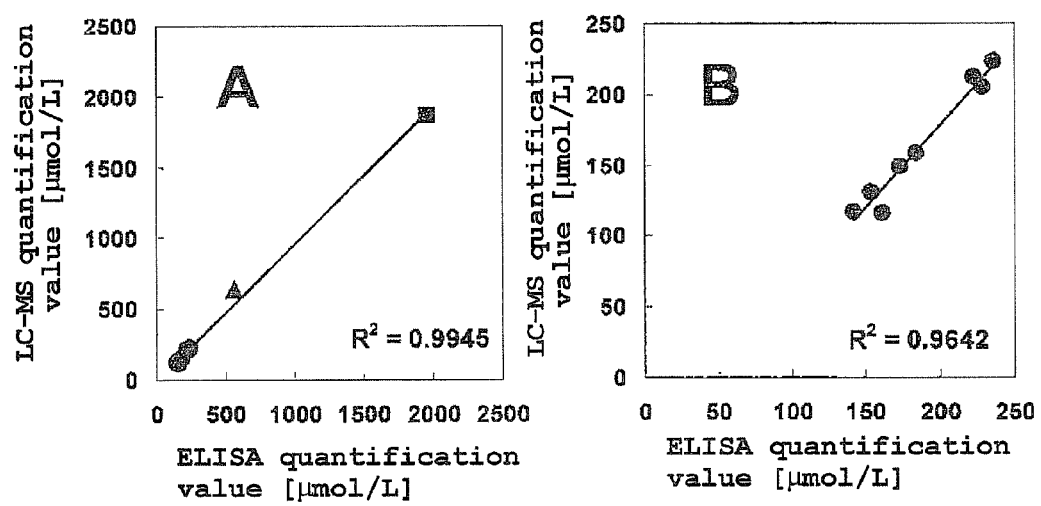
FIG. 4 shows the results of measurement evaluation of the Gly concentration in real samples, wherein A is a graph showing the measured Gly concentrations in Japanese sake (square), FCS (triangle), and rat plasma samples (circle), the horizontal axis shows the Gly concentrations measured by ELISA based on the principle shown in FIG. 2, and the vertical axis shows the Gly concentrations measured by high performance liquid chromatography-mass spectrometer (LC-MS). The $R^2$ value based on the approximate curve of Gly concentration obtained by the both measurement methods was 0.9945. B is a graph showing the measured Gly concentrations in rat plasma samples, wherein the horizontal axis shows the Gly concentrations measured by ELISA as in A, and the vertical axis shows the Gly concentrations measured by LC-MS. The $R^2$ value based on the approximate curve of Gly concentration obtained by both measurement methods was 0.9642.

FIG. 4A shows the plotted results of the measurement values of Gly concentration of Japanese sake, FCS and rat plasma samples, as determined by ELISA and LC-MS. In addition, FIG. 4B shows the plotted results of the measurement value of Gly concentration of only the rat plasma sample, as determined by ELISA and LC-MS. From these results, it was found that the Gly measurement values of the real samples as determined by ELISA were almost the same as the Gly measurement values as determined by LC-MS. Furthermore, straight-line approximation to various real samples was examined to find positive correlation in both FIG. 4A and FIG. 4B (FIG. 4A: $R^2$ value=0.9945, FIG. 4B: $R^2$ value=0.9642). These results show that the Gly quantification value by ELISA is highly accurate.

5-2. Quantification of Phenylalanine (Phe)

As real samples, fetal bovine serum (FCS, Fetal Bovine Serum, manufactured by Invitrogen) and rat plasma sample (SD, female, 20-week-old, manufactured by CHARLES RIVER LABORATORIES JAPAN, INC.) were used, and measurement evaluation of Phe in the samples was performed using an anti-Fmoc-Cys-Phe antibody and an amino acid derivatization reagent. The evaluation was performed by comparing the Phe measurement value determined by ELISA based on the principle of FIG. 2 and the Phe measurement value obtained with high performance liquid chromatography-mass spectrometer (LC-MS; high performance liquid chromatography apparatus; 1100 series (manufactured by Agilent Technologies), mass spectrometer; API3000 (manufactured by Applied Biosystems)).

The protein in the real sample was precipitated by mixing the sample and acetonitrile at 1:1. They were mixed by vortex-stirring for about 15 to 30 sec, and the protein was precipitated by a centrifugation operation. The supernatant after treatment was diluted 1- to 100-fold with PBS solution, and subjected to a derivatization reaction with a biotin-[Fmoc-Cys-NHS] reagent. For the derivatization reaction, acetonitrile (11 µL), 0.1M borate buffer (pH 9, 4 µL), the above-mentioned protein sample (4 µL) and the derivatization reagent biotin-[Fmoc-Cys-NHS] (1 µL) were mixed. They were mixed by vortex-stirring for about 15 to 30 sec, and left to stand at room temperature for 15 min. Then, 0.2% acetic acid solution (20 µL) was added to discontinue the derivatization reaction.

Separately, a Phe standard solution to be used for analytical curve was serially diluted with PBS to fall within the concentration range of 0.1 to 1000 µM, and the Phe standard solution at each concentration and acetonitrile were mixed at 1:1. The Phe standard solution after mixing with acetonitrile was subjected to a derivatization reaction with a biotin-[Fmoc-Cys-NHS] reagent. For the derivatization reaction, acetonitrile (11 µL), 0.1M borate buffer (pH 9, 4 mL), the above-mentioned acetonitrile-mixed Phe standard solution (4 µL) and the derivatization reagent biotin-[Fmoc-Cys-NHS] (1 µL) were mixed. They were mixed by vortex-stirring for about 15 to 30 sec, and left to stand at room temperature for 15 min. Then, 0.2% acetic acid solution (20 µL) was added to discontinue the derivatization reaction. The real sample and Phe standard solution after the derivatization reaction were diluted 2000-fold with 0.1% gelatin-containing PBS solution and subjected to ELISA measurement.

The Phe quantification by ELISA measurement was performed according to the following procedures. First, an anti-Fmoc-Cys-Phe antibody (concentration 0.1 μg/mL) was added by 100 μL to each well of a Protein A/G coating plate, and the plate was left to stand at room temperature for 2 hr. Then, the inside of the well was washed three times with PBST solution to give an anti-Fmoc-Cys-Phe antibody solid-phased plate. To each well of the plate, a real sample or a Phe standard solution (each 100 μL) was added after derivatization reaction and dilution treatment, and the plate was left to stand at room temperature for 1 hr. During this procedure, all wells were tightly sealed with a plate seal. Then, the inside of the well was washed three times with PBST solution, and 100 μL of a streptavidin-HRP conjugate solution diluted to a concentration of 1 μg/mL with an Applie Block/GPB (5/95) mixture was added to each well. After standing at room temperature for 1 hr (during which all wells were tightly sealed with plate seal), the inside of the well was washed three times with PBST solution. Thereafter, each well was washed, and a color developing reaction was performed using an OPD solution.

Figure 6:
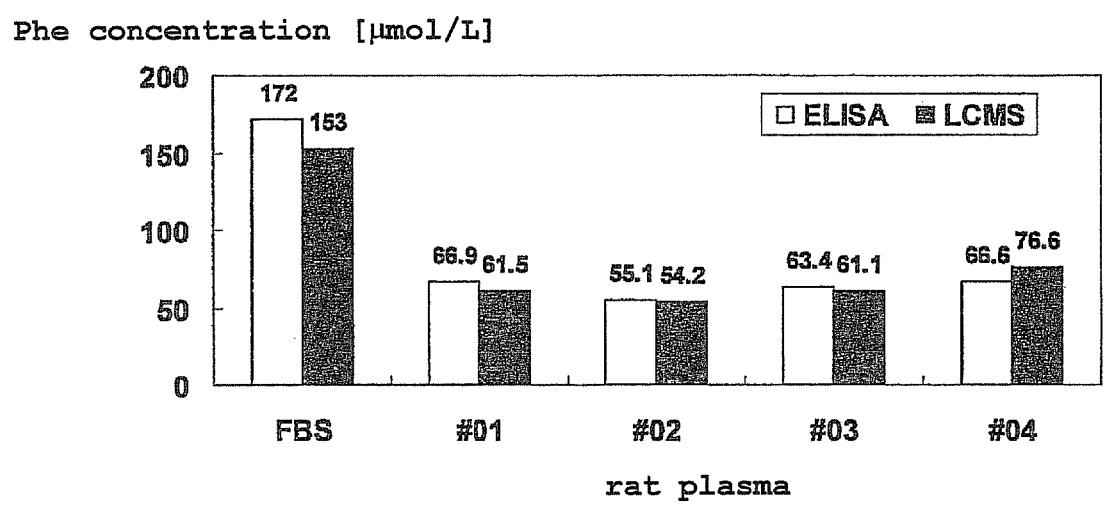
FIG. 6 shows the results of measurement evaluation of the Phe concentration in real samples. The Phe concentration measured by ELISA is shown by a white rod, and that measured by high performance liquid chromatography-mass spectrometer (LC-MS) is shown by a black rod. The vertical axis shows Phe concentration.

FIG. 6 is a graph showing comparison of respective measurement values of Phe concentrations of FCS and rat plasma samples as determined by ELISA and LC-MS. From these results, it was found that the Phe measurement values of the real samples as determined by ELISA were almost the same as the Phe measurement values as determined by LC-MS.

Industrial Applicability

Using the sulfur-containing amino acid derivative of the present invention, a method of measuring an endogenous low-molecular-weight compound specifically and conveniently with high sensitivity is provided. A measurement method using the sulfur-containing amino acid derivative of the present invention can be utilized for test, diagnosis and the like, and is useful in the fields of medical care, food, environment, and the like. Particularly, since amino acids, which are endogenous low-molecular-weight compounds, are a health index of animals, health conditions can be controlled by measuring particular amino acids in the body. Furthermore, hepatopathy may be found by examining the balance of amino acid in the body. Therefore, the measurement of amino acid in the body can lead to the prophylactic medicine or early recognition and early treatment of diseases.

The invention claimed is:

1. An antibody which specifically recognizes the compound represented by the following formula (I):

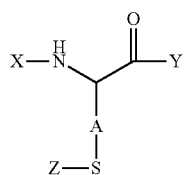

(I)

wherein X is an immunoresponsive hydrophobic group selected from the group consisting of 9-fluorenylmethyloxycarbonyl, quinolinylaminocarbonyl, 4-N,N-dimethylaminosulfonyl-7-piperazino-2,1,3-benzoxadiazole, 4-fluoro-7-nitrobenzo-2-oxa-1,3-diazole, 5-N,N-dimethylaminonaphthalenesulfonyl chloride, o-phthalaldehyde, 4-phenylspiro[furan-2(3H),1'-phthalan]-3,3'-dione, N,N,N-trimethylammonioanilyl N'-hydroxysuccinimidyl carbamate iodide, and fluorescein, Y is a group bound to an endogenous low-molecular-weight compound selected from the group consisting of an amino acid, an organic acid, a sugar, a sugar phosphate, a nucleic acid, a free fatty acid, and an oligopeptide, Z is selected from the group consisting of a hydrogen atom, a high-molecular-weight-imparting group, and a labeling compound modifying group, and A is a single bond or a $C_{1-6}$ alkylene group, wherein the antibody recognizes at least the immunoresponsive hydrophobic group and the endogenous low-molecular-weight compound in the compound of Formula I, wherein said endogenous low-molecular-weight compound has a molecular weight of 1000 or below.

2. The antibody according to claim 1, wherein said antibody is a monoclonal antibody.

3. A method of measuring an endogenous low-molecular-weight compound in a body, comprising:

(A) reacting a sulfur-containing amino acid derivative comprising a structure represented by the following formula (I):

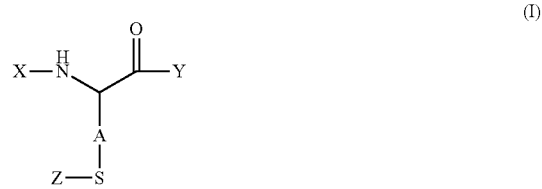

wherein X is an immunoresponsive hydrophobic group, Y is a reactive group reactive to the endogenous low-molecular-weight compound to be measured, Z is a labeling compound modifying group, and A is a single bond or a $C_{1-6}$ alkylene group, with a test sample to form a coupling product of the derivative and the endogenous low-molecular-weight compound, present in the test sample, wherein said coupling product comprises a structure represented by the formula I above, wherein Y is bound to the endogenous low-molecular-weight compound, (B) contacting the coupling product formed in step (A) with the antibody according to claim 1, forming a coupling product-antibody complex, (C) measuring a label bound to the coupling product in the coupling product-antibody complex of step (B).

4. A hybridoma which produces the antibody according to claim 1.

5. A hybridoma which produces the antibody according to claim 2.

6. The antibody according to claim 1, wherein the immunoresponsive hydrophobic group is selected from the group consisting of a 9-fluorenylmethyloxycarbonyl group and a quinolinylaminocarbonyl group.

7. The antibody according to claim 6, wherein said antibody is a monoclonal antibody.

8. A hybridoma which produces the antibody according to claim 7.

9. A method of producing the antibody according to claim 1, comprising immunizing an animal with an antigen comprising a compound represented by the following formula (I):

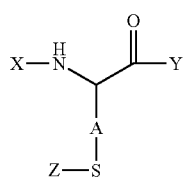 (I)

wherein X is an immunoresponsive hydrophobic group selected from the group consisting of 9-fluorenylmethyloxycarbonyl, quinolinylaminocarbonyl, 4-N,N-dimethylaminosulfonyl-7-piperazino-2,1,3-benzoxadiazole, 4-fluoro-7-nitrobenzo-2-oxa-1,3-diazole, 5-N,N-dimethylaminonaphthalenesulfonyl chloride, o-phthalaldehyde, 4-phenylspirorfuran-2(3H),1'-phthalan1-3,3'-dione, N,N,N-trimethylammonioanilyl N'-hydroxysuccinimidyl carbamate iodide, and fluorescein, Y is a group bound to an endogenous low-molecular-weight compound selected from the group consisting of an amino acid, an organic acid, a sugar, a sugar phosphate, a nucleic acid, a free fatty acid, and an oligopeptide, Z is an immunogenic carrier protein, and A is a single bond or a $C_{1-6}$alkylene group, wherein the antibody recognizes at least the immunoresponsive hydrophobic group and the endogenous low-molecular-weight compound in the compound of Formula I, wherein said endogenous low-molecular-weight compound has a molecular weight of 1000 or below.

\* \* \* \* \*

UNITED STATES PATENT AND TRADEMARK OFFICE
CERTIFICATE OF CORRECTION

PATENT NO. : 9,127,039 B2
APPLICATION NO. : 13/678805
DATED : September 8, 2015
INVENTOR(S) : Kubota et al.

It is certified that error appears in the above-identified patent and that said Letters Patent is hereby corrected as shown below:

At Column 38, line 65 to Column 39, line 29, please amend Claim 9 as follows.

9. A method of producing the antibody according to claim 11, comprising immunizing an animal with an antigen comprising a compound represented by the following formula (I):

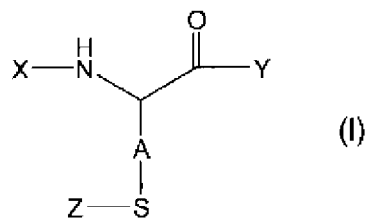

wherein X is an immunoresponsive hydrophobic group selected from the group consisting of 9-fluorenylmethyloxycarbonyl, quinolinylaminocarbonyl, 4-N,N-dimethylaminosulfonyl-7-piperazino-2,1,3-benzoxadiazole, 4-fluoro-7-nitrobenzo-2-oxa-1,3-diazole, 5-N,N-dimethylaminonaphthalenesulfonyl chloride, o-phthalaldehyde, 4-phenylspiro[furan-2(3H),1'-phthalan]-3,3'-dione, N,N,N-trimethylammonioanilyl N'-hydroxysuccinimidyl carbamate iodide, and fluorescein, Y is a group bound to an endogenous low-molecular-weight compound selected from the group consisting of an amino acid, an organic acid, a sugar, a sugar phosphate, a nucleic acid, a free fatty acid, and an oligopeptide, Z is an immunogenic carrier protein, and A is a single bond or a $C_{1-6}$ alkylene group, wherein the antibody recognizes at least the immunoresponsive hydrophobic group and the endogenous low-molecular-weight compound in the compound of Formula I, wherein said endogenous low-molecular-weight compound has a molecular weight of 1000 or below.

Signed and Sealed this
Sixteenth Day of August, 2016

Michelle K. Lee
*Director of the United States Patent and Trademark Office*